(12) United States Patent
Kim et al.

(10) Patent No.: US 11,510,582 B2
(45) Date of Patent: Nov. 29, 2022

(54) METHOD FOR GUIDING MEASUREMENT OF BIOLOGICAL SIGNAL IN WEARABLE DEVICE

(71) Applicant: Samsung Electronics Co., Ltd., Gyeonggi-do (KR)

(72) Inventors: Minji Kim, Gyeonggi-do (KR); Hyejung Seo, Gyeonggi-do (KR); Seongmin Je, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 501 days.

(21) Appl. No.: 16/580,409

(22) Filed: Sep. 24, 2019

(65) Prior Publication Data

US 2020/0170522 A1 Jun. 4, 2020

(30) Foreign Application Priority Data

Dec. 4, 2018 (KR) .................. 10-2018-0154619

(51) Int. Cl.
*A61B 5/00* (2006.01)
*A61B 5/024* (2006.01)
*G06F 1/16* (2006.01)
*A61B 5/145* (2006.01)

(52) U.S. Cl.
CPC .......... *A61B 5/02427* (2013.01); *G06F 1/163* (2013.01); *A61B 5/14532* (2013.01); *A61B 5/7465* (2013.01)

(58) Field of Classification Search
None
See application file for complete search history.

(56) References Cited

U.S. PATENT DOCUMENTS

| 6,990,365 | B1 | 1/2006 | Parker et al. |
| 7,424,317 | B2 | 9/2008 | Parker et al. |
| 7,774,037 | B2 | 8/2010 | Parker et al. |
| 8,092,386 | B1 * | 1/2012 | Wenzel ............ A61M 5/14276 600/323 |

(Continued)

FOREIGN PATENT DOCUMENTS

| EP | 3106085 A1 | 12/2016 |
| KR | 10-2017-0019745 A | 2/2017 |

(Continued)

OTHER PUBLICATIONS

International Search Report dated Jan. 15, 2020.
European Search Report dated Apr. 9, 2020.

*Primary Examiner* — Shirley X Jian
(74) *Attorney, Agent, or Firm* — Cha & Reiter, LLC

(57) ABSTRACT

An electronic device may include a display, a photoplethysmogram (PPG) sensor, a wireless communication circuit, a processor operatively connected to the display, the PPG sensor, and the wireless communication circuit, and a memory operatively connected to the processor. The electronic device implements the method, including monitoring blood glucose values of a user using the PPG sensor, displaying a notification prompting the user to measure blood glucose values using an external electronic device based at least partially on the monitored blood glucose values, and receive additional blood glucose values measured by the external electronic device using the wireless communication circuit.

13 Claims, 16 Drawing Sheets

(56) References Cited

U.S. PATENT DOCUMENTS

| | | | |
|---|---|---|---|
| 8,417,312 B2* | 4/2013 | Kamath | A61B 5/14532 |
| | | | 600/347 |
| 8,517,941 B1* | 8/2013 | Wenzel | A61B 5/14503 |
| | | | 600/365 |
| 8,630,692 B2* | 1/2014 | Wenzel | A61B 5/0006 |
| | | | 600/509 |
| 8,718,965 B2* | 5/2014 | Hayter | A61M 5/1723 |
| | | | 600/365 |
| 9,044,149 B2* | 6/2015 | Richards | A61B 5/0022 |
| 9,044,171 B2* | 6/2015 | Venkatraman | A61B 5/389 |
| 9,962,082 B2 | 5/2018 | Kim et al. | |
| 10,209,365 B2 | 2/2019 | Venkatraman et al. | |
| 10,231,675 B2 | 3/2019 | Chung et al. | |
| 2004/0133081 A1 | 7/2004 | Teller et al. | |
| 2004/0152957 A1 | 8/2004 | Stivoric et al. | |
| 2005/0054907 A1 | 3/2005 | Page et al. | |
| 2005/0131286 A1 | 6/2005 | Parker et al. | |
| 2005/0192488 A1 | 9/2005 | Bryenton et al. | |
| 2008/0132771 A1 | 6/2008 | Parker et al. | |
| 2009/0005663 A1 | 1/2009 | Parker et al. | |
| 2010/0004517 A1 | 1/2010 | Bryenton et al. | |
| 2010/0004522 A1 | 1/2010 | Varela | |
| 2010/0280348 A1* | 11/2010 | Wenzel | A61B 5/14551 |
| | | | 600/365 |
| 2014/0275850 A1* | 9/2014 | Venkatraman | A61B 5/02416 |
| | | | 600/595 |
| 2014/0288435 A1* | 9/2014 | Richards | A61B 5/0205 |
| | | | 600/479 |
| 2015/0190098 A1 | 7/2015 | Patek et al. | |
| 2015/0230735 A1 | 8/2015 | Venkatraman et al. | |
| 2017/0215811 A1* | 8/2017 | Newberry | A61B 5/14532 |
| 2017/0347894 A1 | 12/2017 | Bhushan et al. | |
| 2018/0055454 A1* | 3/2018 | Newberry | A61B 5/14551 |
| 2018/0344259 A1 | 12/2018 | Pavlov et al. | |
| 2019/0150854 A1 | 5/2019 | Chung et al. | |
| 2020/0060585 A1* | 2/2020 | Harris | A61B 5/6829 |
| 2020/0155081 A1* | 5/2020 | Seo | A61B 5/742 |

FOREIGN PATENT DOCUMENTS

| | | |
|---|---|---|
| KR | 10-2017-0055409 A | 5/2017 |
| WO | 2004/032715 A2 | 4/2004 |
| WO | 2005/077260 A1 | 8/2005 |
| WO | 2013/032965 A1 | 3/2013 |
| WO | 2016/080911 A1 | 5/2016 |

* cited by examiner

METHOD FOR GUIDING MEASUREMENT OF BIOLOGICAL SIGNAL IN WEARABLE DEVICE

CROSS-REFERENCE TO RELATED APPLICATION(S)

This application is based on and claims priority under 35 U.S.C. § 119 to Korean Patent Application No. 10-2018-0154619, filed on Dec. 4, 2018, in the Korean Intellectual Property Office, the disclosure of which is incorporated by reference herein its entirety.

BACKGROUND

1. Field

The disclosure relates to a method for guiding a measurement of a biological signal in a wearable device.

2. Description of Related Art

An electronic device may measure a user's biological signal using a sensor. The biological signal may include, for example, at least one of heart rate, oxygen saturation, blood pressure, and/or blood glucose. Because the biological signal may be serve as a health indicator, measurement may be required at regular intervals of time. For example, because the blood glucose may be predictably maximal at a set time after a meal (e.g., 30 minutes to 2 hours), and may be predictably minimal when there user has not eaten and the stomach is empty, the user of the electronic device may be required to measure blood glucose at a predetermined time following meal, or a longer predetermined time in which the user is predicted to have no food content in the stomach. In another example, when the blood pressure is equal to or higher than a critical value for a predetermined after an end of an exercise time (e.g., within 2 minutes), the incidence of stroke may increase. Therefore, the user may be required to measure blood pressure after terminating physical exercise.

The above information is presented as background information only to assist with an understanding of the disclosure. No determination has been made, and no assertion is made, as to whether any of the above might be applicable as prior art with regard to the disclosure.

SUMMARY

Methods for measuring a biological signal may vary. For example, an electronic device may measure the biological signal by collecting venous or capillary blood of a user, and/or measure the biological signal by an optical or electrical method, without blood collection.

A blood analyzer that collects the venous blood, or a self-monitoring blood glucose measurement device (SMBG) that collects the capillary blood may both accurately measure a biological signal (e.g., a blood glucose) from the blood of the user. However, because the blood collection process involves the discomfort of pain for a user, and the blood analyzer is typically not very portable, the continuous measurement of blood sugar can be limited or impeded.

When the electronic device includes a wearable device coupled to a body part of the user, the electronic device may continuously monitor the biological signal using a biometric information sensor, such as a photoplethysmogram (PPG) sensor. However, because of the limitations on a physical size of the wearable device, the measurement accuracy of the biometric information sensor in the wearable device may be lower than that of other comparable electronic devices (e.g., the blood analyzer or the self-monitoring blood glucose measurement).

Certain embodiments disclosed in the disclosure may provide a method for continuously monitoring the biological signal using the wearable device and for increasing the accuracy of the measurement.

Aspects of the disclosure are to address at least the above-mentioned problems and/or disadvantages and to provide at least the advantages described below. Accordingly, an aspect of the disclosure is to provide an electronic device including a housing, a display visible through a first portion of the housing, a photoplethysmogram (PPG) sensor exposed through a second portion of the housing, a wireless communication circuit, a processor operatively connected to the display, the PPG sensor, and the wireless communication circuit, and a memory operatively connected to the processor, wherein the memory stores instructions executable by the processor to cause the electronic device to: detect a first blood glucose value using the PPG sensor, based at least in part on the detected first blood glucose value, display a notification on the display prompting measurement of blood glucose using an external electronic device, and receive a transmission through the wireless communication circuit of a second blood glucose value as detected by the external electronic device.

Accordingly, another aspect of the disclosure is to provide a method for a wearable device, including when the wearable electronic device is coupled to a body part of a user, detecting a first blood glucose value using the PPG sensor, based at least in part on the detected first blood glucose value, displaying a notification on a display prompting measurement of blood glucose using an external electronic device, and receiving a transmission through a wireless communication circuit of a second blood glucose value, as detected by the external electronic device.

Accordingly, another aspect of the disclosure is to provide a wearable device capable of being worn on a body part of a user including at least one attachment member capable of being detached from the body part of the user, a housing coupled to the at least one attachment member, a display visible through a first portion of the housing, a photoplethysmogram (PPG) sensor exposed through a second portion of the housing opposite to the first portion, a wireless communication circuit included in the housing, a processor operatively connected to the display, the PPG sensor, and the wireless communication circuit, and a memory operatively coupled to the processor, wherein the memory stores instructions executable by the processor to cause the wearable device to: detect first blood glucose values using the PPG sensor, control the display to display a notification prompting measurement of second blood glucose values using an external electronic device at least partially based on the detected first blood glucose values, receive a transmission of the second blood glucose values as detected by the external electronic device using the wireless communication circuit, and calibrate the PPG sensor based at least partially on the received second blood glucose values.

Other aspects, advantages, and salient features of the disclosure will become apparent to those skilled in the art from the following detailed description, which, taken in conjunction with the annexed drawings, discloses certain embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

In the description of the drawings, the same or similar reference numerals may be used for the same or similar components.

DETAILED DESCRIPTION

Hereinafter, certain embodiments of the disclosure will be described with reference to accompanying drawings. Certain embodiments of the disclosure used herein are not intended to limit the disclosure to specific embodiments, and it should be understood that the embodiments include modification, equivalent, and/or alternative on the corresponding embodiments described herein.

Figure 1:
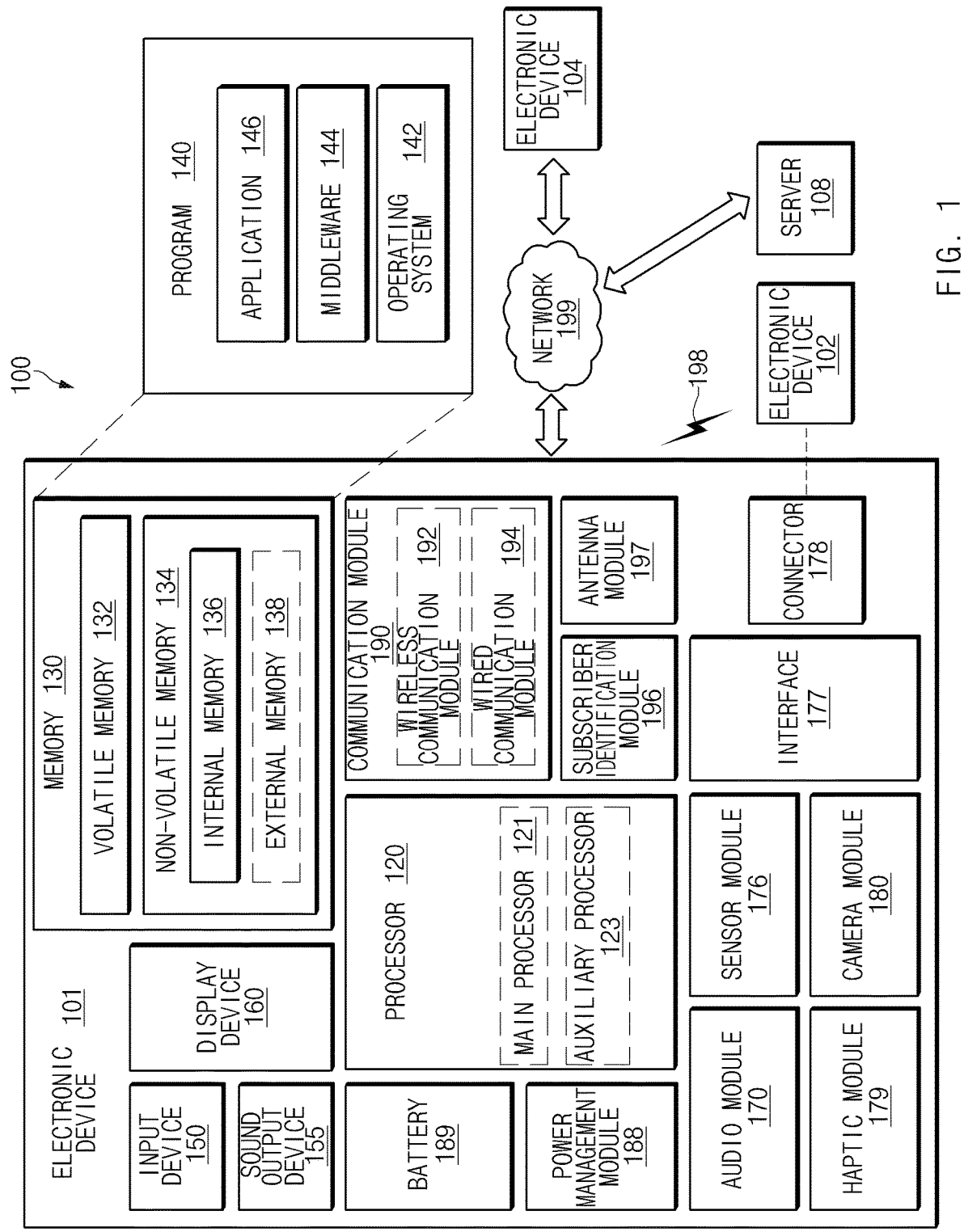
FIG. 1 is a block diagram illustrating an electronic device in a network environment according to certain embodiments.

FIG. 1 is a block diagram illustrating an electronic device 101 in a network environment 100 according to certain embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a predetermined function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more predetermined protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element implemented using a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
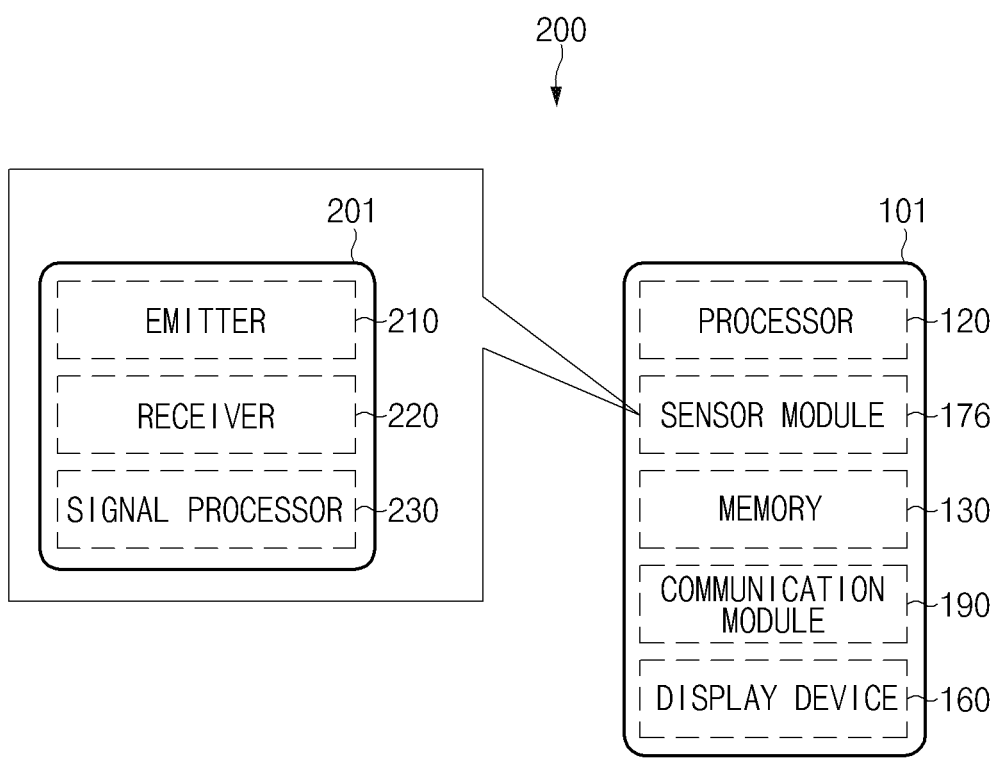
FIG. 2 illustrates a block diagram of an electronic device and a biometric information sensor according to certain embodiments.

FIG. 2 illustrates a block diagram 200 of the electronic device 101 and a biometric information sensor 201 according to certain embodiments.

Referring to FIG. 2, the electronic device 101 may include at least one of the processor 120, the sensor module 176, the memory 130, the communication module 190, or the display device 160. In the following, unless otherwise defined, a description of a component having the same reference numeral may be referenced by the description set forth above in connection with FIG. 1. For convenience of explanation, redundant description is omitted. The components of the electronic device 101 illustrated in FIG. 2 are illustrative, and the electronic device 101 may not include some components illustrated in FIG. 2 or may further include components not illustrated in FIG. 2.

According to certain embodiments, the processor 120 may be configured to be electrically or operatively coupled to other components (e.g., at least one of the sensor module 176, the memory 130, the communication module 190, or the display device 160) of the electronic device 101 and to control other components of the electronic device 101. In following embodiments, an operation of the electronic device 101 may be referenced as an operation of the processor 120.

According to certain embodiments, the memory 130 may be electrically connected to the processor 120 and may store at least one instruction that causes the processor 120 to perform various operations. In following embodiments, the operation of the processor 120 may be performed based on the instructions stored in the memory 130.

According to certain embodiments, the display device 160 may include a display. According to an embodiment, the display may be configured to provide visual information to the user and receive user input (e.g., touch input). According to an embodiment, an indicator is configured to generate light having at least one wavelength via a front surface (e.g., a surface on which the display of the electronic device 101 is located) of a housing of the electronic device 101. According to an embodiment, the display device 160 includes a plurality of pixels, and at least some of the plurality of pixels may be used as an emitter 210 of the sensor module 176.

According to certain embodiments, the communication module 190 may be configured to communicate with an external electronic device (e.g., the electronic device 102, the electronic device 104, or the server 108 in FIG. 1) via a network (e.g., the first network 198 and/or the second network 199 in FIG. 1). According to an embodiment, the processor 120 may use the communication module 190 to transmit information associated with the electronic device 101 to the external electronic device. For example, the electronic device 101 may use the communication module 190 to transmit data sensed by the biometric information sensor 201 to an external electronic device.

According to certain embodiments, the sensor module 176 may include at least one sensor for sensing information associated with an ambient environment of the electronic device 101 and/or an external object (e.g., user or the like). According to an embodiment, the sensor module 176 may include at least one of the proximity sensor, the biometric information sensor 201, or a motion sensor. For example, the proximity sensor may be located at the front surface of the housing of the electronic device 101 and may sense a presence of the external object located within a predetermined range from the proximity sensor. For example, the motion sensor may be located within the housing of the electronic device 101 and may include at least one sensor (gyro sensor and/or acceleration sensor, or the like) for sensing at least one of a posture, a tilt, or a movement of the electronic device 101.

According to certain embodiments, the biometric information sensor 201 may include the emitter 210, a receiver 220, and/or a signal processor 230 (or a signal processing circuit). According to an embodiment, the processor 120 may use the biometric information sensor 201 to measure a biological signal (e.g., at least one of heart rate, oxygen saturation, blood pressure, or blood glucose) associated with the external object (e.g., user or the like). For example, the biometric information sensor 201 may include a photoplethysmogram (PPG) sensor.

According to certain embodiments, the emitter 210 may include at least one light emitting element (e.g., a light emitting diode, LED) for illuminating light of a wavelength within a predetermined range. According to an embodiment, the emitter 210 may include at least one light emitting element for emitting (or outputting) light having a wavelength within a predetermined range (e.g., 400 nm to 1000 μm). According to an embodiment, the emitter 210 may include a plurality of light emitting elements for illuminating light-beams corresponding to a plurality of wavelengths. For example, the emitter 210 may include a plurality of light emitting elements respectively corresponding to red (wavelength: 600 to 700 nm), green (wavelength: 500 to 600 nm), blue (wavelength: 400 to 500 nm), and/or infrared ray (wavelength: 780 to 1000 m). In another example, the emitter 210 may include a spectrometer (spectrography) capable of selectively adjusting a wavelength. According to an embodiment, the emitter 210 may be implemented on the display device 160. For example, at least a portion of the emitter 210 may be implemented using pixels or sub-pixels of the display device 160.

According to certain embodiments, the receiver 220 may include at least one light receiving element for sensing light. According to an embodiment, the light receiving element may detect light of a predetermined wavelength and sense an intensity of the detected light. For example, the light receiving element may output a current signal having a magnitude corresponding to the intensity of the detected light. For example, the light receiving element may include a photo detector or a photo diode. The photo diode is an example of the photo detector, and the light receiving element of the disclosure may be any element capable of sensing the light. According to an embodiment, the receiver 220 may include at least one photo detector (e.g., photo diode) for sensing light having a wavelength within at least a predetermined range (e.g., 400 to 1000 μm). According to an embodiment, the receiver 220 may include a plurality of light receiving elements for sensing light-beams corresponding to a plurality of wavelengths. For example, the receiver 220 may include a plurality of photo detectors configured to detect light-beams corresponding to red, green, blue, and/or infrared ray, respectively.

According to certain embodiments, the signal processor 230 may control the emitter 210 and the receiver 220. For example, the signal processor 230 may control the emitter 210 and/or the receiver 220 under a control of the processor 120. According to an embodiment, the signal processor 230 may drive at least one LED of the emitter 210. According to an embodiment, the signal processor 230 may process a signal sensed by the receiver 220. For example, the signal processor 230 may convert a current signal sensed by the receiver 220 into a voltage signal, process (e.g., amplify and/or filter) the voltage signal, and convert the processed voltage signal into a digital signal. According to an embodiment, the signal processor 230 may include a memory for storing biometric information sensed by the receiver 220 and/or instructions for controlling the receiver 220 and the emitter 210. According to an embodiment, the processor 120 may perform post processing (e.g., filtering and/or noise cancellation) on the biometric information sensed by the biometric information sensor 201.

According to certain embodiments, the biometric information sensor 201 may illuminate light one surface (e.g., rear surface or front surface) of the electronic device 101 and receive (e.g., sense or detect) the light reflected from the external object (e.g., user). For example, the biometric information sensor 201 may sense the light or output the light via a window having a light-transmitting property formed on at least a portion of the housing of the electronic device 101.

Figure 3A:
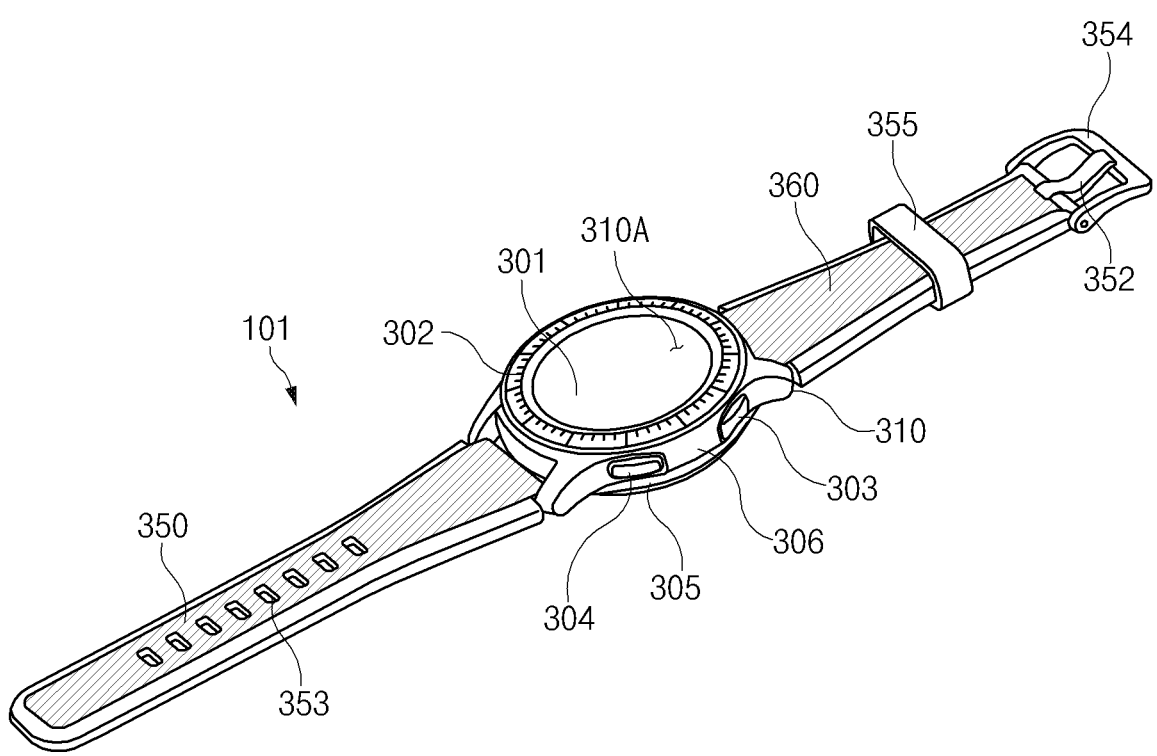
FIG. 3A is a perspective view of a front face of an electronic device according to an embodiment.

FIG. 3A is a perspective view of a front face of the electronic device 101 according to an embodiment. Further, FIG. 3B is a perspective view of a rear face of the electronic device 101.

Figure 3B:
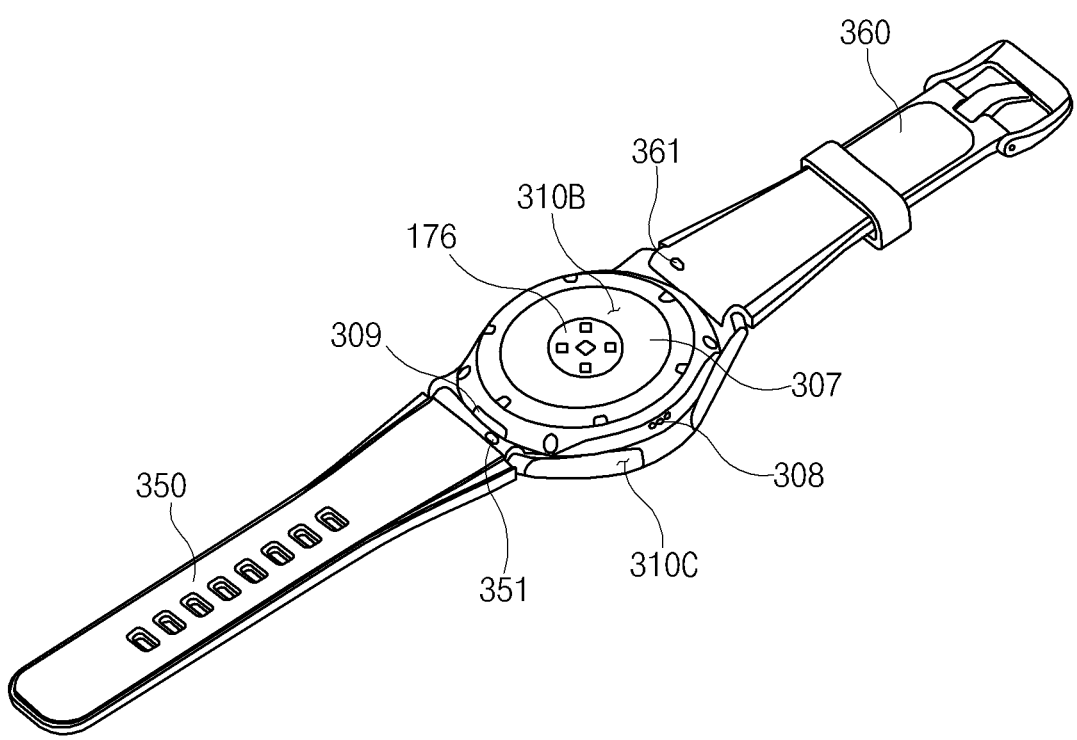
FIG. 3B is a perspective view of a rear face of an electronic device in FIG. 3A.

Referring to FIGS. 3A and 3B, the electronic device 101 according to an embodiment may include a housing 310 including a first surface (or front face) 310A, a second surface (or rear surface) 310B, and a side surface 310C surrounding a space between the first surface 310A and the second surface 310B, and attachment members 350 and 360 connected to at least a portion of the housing 310 and configured to detachably attach the electronic device 101 to a body part (e.g., a wrist, an ankle, or the like) of the user. In another embodiment (not shown), the housing may refer to a structure forming some of the first surface 310A, the second surface 310B, and the side surface 310C in FIG. 3A. According to an embodiment, the first surface 310A may be formed by a front surface plate 301 (e.g., a glass plate or a polymer plate including a variety of coating layers) having at least a portion substantially transparent. The second surface 310B may be formed by a substantially opaque rear surface plate 307. A rear surface plate 307 may be formed, for example, by a coated or colored glass, a ceramic, a polymer, a metal (e.g., aluminum, stainless steel (STS), or magnesium), or a combination of at least two of the above materials. The side surface 310C is formed by a side surface bezel structure (or a "side surface member") 306 that is coupled to the front surface plate 301 and the rear surface plate 307 and contains a metal and/or a polymer. In some embodiments, the rear surface plate 307 and the side surface bezel structure 306 may be integrally formed and contain the same material (e.g., a metal material such as aluminum). The attachment member 350 and 360 may be formed of various materials and shapes. By a woven material, a leather, a rubber, a urethane, a metal, a ceramic, or a combination of at least two of the above-mentioned materials, an integrated unit link may be formed or a plurality of unit links may be formed to be movable to each other.

According to an embodiment, the electronic device 101 may include at least one of a display (e.g., 320 in FIG. 4A or at least a portion of the display device 160), an audio module disposed in microphone holes 305 and/or 308 (e.g., at least a portion of the display device 160 in FIG. 1), the sensor module 176, a key input device 302, 303, and 304, or a connector hole 309. In some embodiments, the electronic device 101 may omit at least one of the components (e.g., the key input device 302, 303, and 304, the connector hole 309, or the sensor module 176) or may further include another component.

The display 320 may be exposed through a substantial portion of the front surface plate 301, for example. A shape of the display 320 may be a shape corresponding to a shape of the front surface plate 301, and may be various shapes such as a circle, an ellipse, a polygon, or the like. The display 320 may be disposed to be coupled with or adjacent to a touch sensing circuit, a pressure sensor capable of measuring an intensity (pressure) of a touch, and/or a fingerprint sensor.

The audio module disposed in the microphone holes 305 and 308 may include the microphone hole 305 and the speaker hole 308. The microphone hole 305 may include a microphone therein for acquiring an external sound. Further, in some embodiments, a plurality of microphones may be arranged in the microphone hole 305 to sense a direction of a sound. The speaker hole 308 may be used as an external speaker and a receiver for a call. In some embodiments, the speaker hole 308 and the microphone hole 305 may be implemented as a single hole, or a speaker (e.g., a piezo speaker) may be included without the speaker hole 308.

The sensor module 176 may generate an electrical signal or data value corresponding to an internal operational state of the electronic device 101 or an external environmental condition. The sensor module 176 may include the biometric sensor module 176 (e.g., HRM sensor) disposed on the second surface 310B of the housing 310, for example. The electronic device 101 may further include a sensor module (not shown), for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input device 302, 303, and 304 may include the wheel key 302 disposed on the first surface 310A of the housing 310 and rotatable in at least one direction, and/or the side key button 303 and 304 disposed on the side surface 310C of the housing 310. The wheel key may be in a form corresponding to the shape of the front surface plate 301. In another embodiment, the electronic device 101 may not include some or all of the above-mentioned key input device 302, 303, and 304, and the non-included key input device 302, 303, and 304 may be implemented in another form, such as a soft key or the like. The connector hole 309 may receive therein a connector (e.g., a USB connector) for transmitting and receiving power and/or data with the external electronic device. Another connector hole (not shown) that may receive therein a connector for transmitting and receiving an audio signal with the external electronic device may be included. The electronic device 101 may further include, for example, a connector cover (not shown) for covering at least a portion of the connector hole 309 and blocking an entry of external foreign matter into the connector hole.

The attachment member 350 and 360 may be detachably attached to at least a portion of the housing 310 using locking members 351 and 361. The attachment members 350 and 360 may include at least one of a fixing member 352, a fixing member fastening hole 353, a band guide member 354 and a band fixing ring 355.

The fixing member 352 may be configured to fix the housing 310 and the attachment members 350 and 360 to the body part (e.g., the wrist, ankle, or the like) of the user. The fixing member fastening hole 353 may correspond to the fixing member 352 to fix the housing 310 and the attachment members 350 and 360 to the body part of the user. The band guide member 354 may be configured to limit a range of movement of the fixing member 352 when the fixing member 352 and the fixing member fastening hole 353 are fastened with each other. Therefore, the attachment members 350 and 360 may be closely attached to the body part of the user. The band fixing ring 355 may limit a range of movement of the attachment members 350 and 360 while in a state in which the fixing member 352 and the fixing member fastening hole 353 are fastened with each other.

Figure 4A:
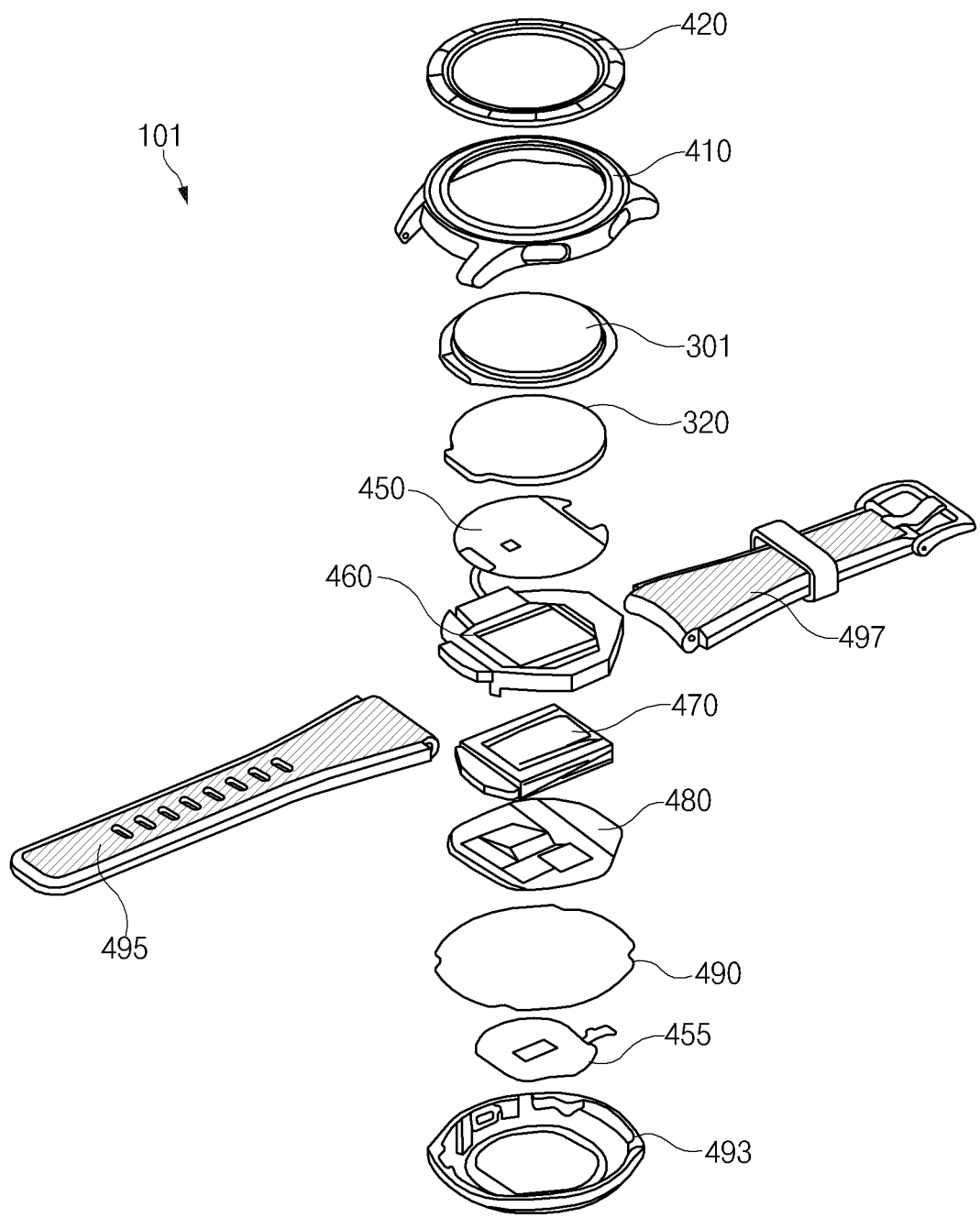
FIG. 4A is an exploded perspective view of an electronic device in FIG. 3A.

FIG. 4A is an exploded perspective view of the electronic device 101.

Referring to FIG. 4A, the electronic device 101 may include a side surface bezel structure 410, a wheel key 420, the front surface plate 301, the display 320, a first antenna 450, a second antenna 455, a support member 460 (e.g., a bracket), a battery 470, a printed circuit board 480, a sealing member 490, a rear surface plate 493, and attachment members 495 and 497. At least one of the components of the electronic device 101 may be the same as or similar to at least one of the components of the electronic device 101 in FIG. 3A or FIG. 3B, and a redundant description thereof will be omitted below. The support member 460 may be disposed within the electronic device 101 and connected to the side surface bezel structure 410 or may be integrally formed with the side surface bezel structure 410. The support member 460 may be formed of, for example, a metal material and/or a non-metal (e.g., a polymer) material. The display 320 may be coupled to one surface of the support member 460 and the printed circuit board 480 may be coupled to the other surface thereof. The printed circuit board 480 may be equipped with a processor, a memory, and/or an interface. The processor may include, for example, at least one of a central processing unit, an application processor, a graphic processing unit (GPU), an application processor sensor processor, or a communications processor.

The memory may include, for example, a volatile memory or a non-volatile memory. The interface may include, for example, a high definition multimedia interface (HDMI), a universal serial bus (USB) interface, an SD card interface, and/or an audio interface. The interface may, for example, electrically or physically couple the electronic device 101 with the external electronic device and include a USB connector, an SD card/MMC connector, or an audio connector.

The battery 470 is a device for supplying power to at least one component of the electronic device 101. The battery 470 may include, for example, a non-rechargeable primary battery, a rechargeable secondary battery, or a fuel cell. At least a portion of the battery 470 may be disposed substantially coplanar with the printed circuit board 480, for example. The battery 470 may be disposed integrally within the electronic device 101 and may be detachably disposed with the electronic device 101.

The first antenna 450 may be disposed between the display 320 and the support member 460. The first antenna 450 may include, for example, a near field communication (NFC) antenna, a wireless charging antenna, and/or a magnetic secure transmission (MST) antenna. The first antenna 450 may, for example, be in short-range communication with the external device, wirelessly transmit and receive power utilized for charging, and transmit a magnetic-based signal including a short-range communication signal or payment data. In another embodiment, an antenna structure may be formed by the side surface bezel structure 410 and/or a portion of the support member 460, or a combination thereof.

The second antenna 455 may be disposed between the printed circuit board 480 and the rear surface plate 493. The second antenna 455 may include, for example, a near field communication (NFC) antenna, a wireless charging antenna, and/or a magnetic secure transmission (MST) antenna. The second antenna 455 may, for example, be in short-range communication with the external device, wirelessly transmit and receive power utilized for charging, and transmit a magnetic-based signal including a short-range communication signal or payment data. In another embodiment, an antenna structure may be formed by a portion of the side surface bezel structure 410 and/or a rear surface plate 493, or a combination thereof.

The sealing member 490 may be positioned between the side surface bezel structure 410 and the rear surface plate 493. The sealing member 490 may be configured to block moisture and foreign matter from entering a space surrounded by the side surface bezel structure 410 and the rear surface plate 493 from the outside.

Figure 4B:
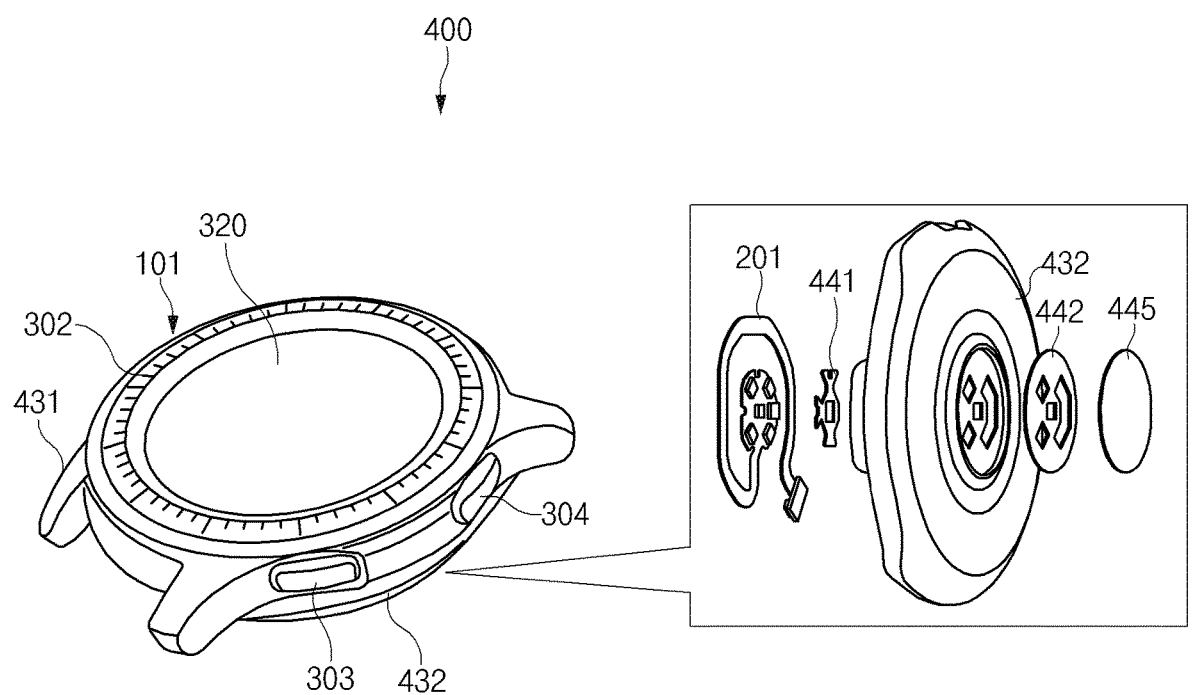
FIG. 4B illustrates a mounting structure of a biometric information sensor of an electronic device according to certain embodiments.

FIG. 4B illustrates a mounting structure 400 of the biometric information sensor 201 of the electronic device 101 according to certain embodiments.

According to certain embodiments, an electronic device (e.g., the electronic device 101 in FIG. 2) may include a front surface housing 431 and a rear surface housing 432. For example, the front surface housing 431 and the rear surface housing 432 may correspond to the housing 310 in FIG. 3A. According to an embodiment, the display 320 (e.g., the display device 160 in FIG. 2) may be exposed through one surface of the front surface housing 431. The key input device 302, 303, and 304 may be located on at least a portion of the front surface housing 431.

According to an embodiment, a biometric information sensor (e.g., the biometric information sensor 201 in FIG. 2) may be located on one surface of the rear surface housing 432. For example, a first structure 441 may be positioned between the biometric information sensor 201 and the rear surface housing 432. The first structure 441 may be used to fix the biometric information sensor 201 to the rear surface housing 432. The first structure 441 may be used to adjust a spacing between the biometric information sensor 201 and a cover glass 445.

According to an embodiment, the biometric information sensor 201 may be configured to illuminate light through the cover glass 445 located on one surface of the rear surface housing 432 and receive the reflected light to acquire biometric information. For example, the cover glass 445 may be made of a light-transmitting material.

According to an embodiment, a second structure 442 may be positioned between the cover glass 445 and the rear surface housing 432. For example, the second structure 442 may be used to protect elements of the biometric information sensor 201. The second structure 442 may be made of a light-absorbing material or may have a light-absorbing color. The second structure 442 may be used to reduce noise due to light reflection. The second structure 442 may be used as a barrier structure. For example, the second structure 442 may be used for crosstalk reduction.

Figure 5:
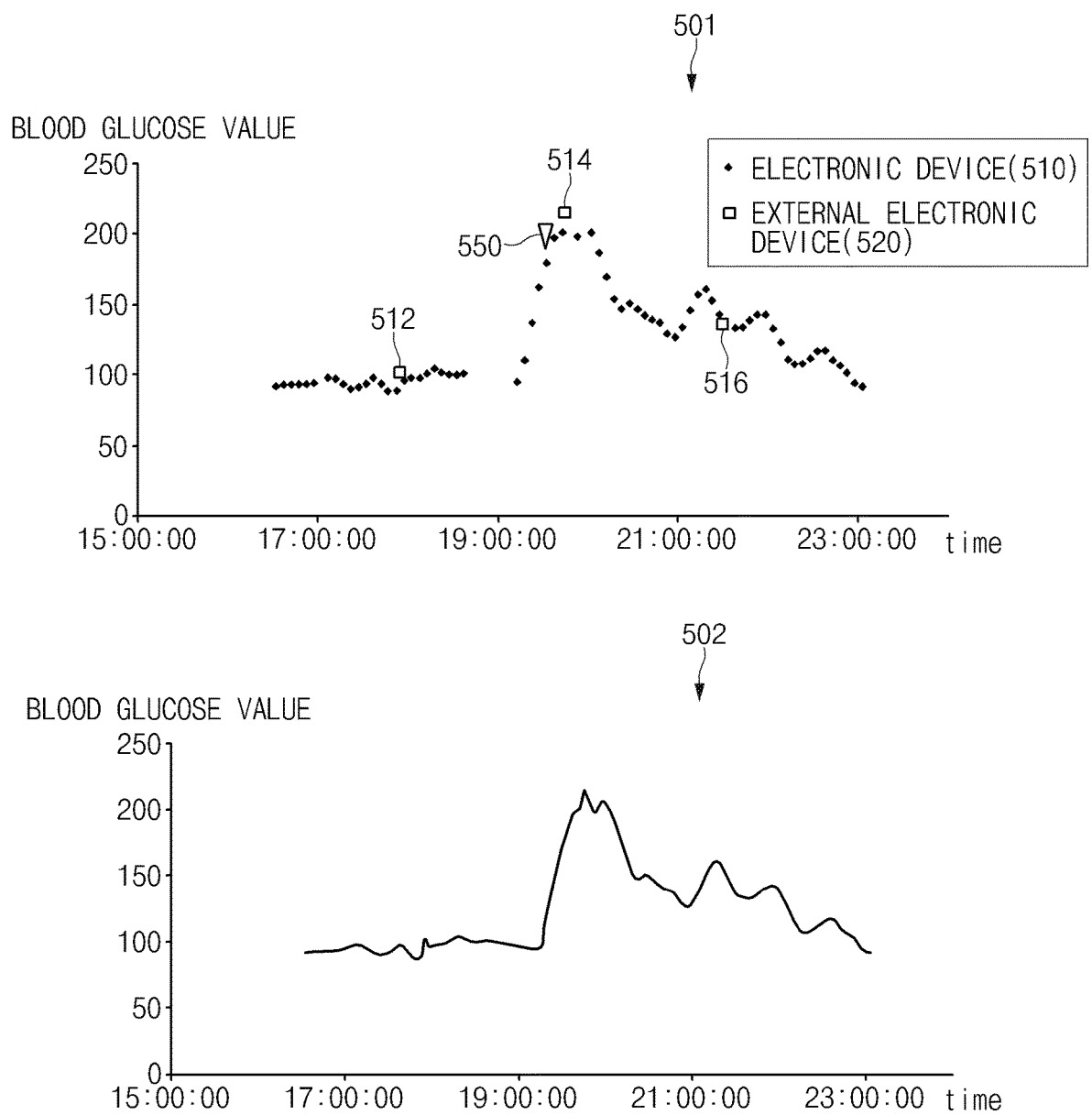
FIG. 5 illustrates graphs illustrating blood glucose values according to certain embodiments.

FIG. 5 illustrates graphs 501 and 502 illustrating blood glucose values according to certain embodiments.

Referring to FIG. 5, a first graph 501 may represent blood glucose values measured by the electronic device 101. Further, a second graph 502 may represent values of the blood glucose values of the first graph 501 calibrated based on blood glucose values measured by the external electronic device. A horizontal axis of the graphs 501 and 502 may represent a time (unit: hour: minute: second), and a vertical axis thereof may represent a blood glucose value (unit: mg/dL). In the first graph 501, first blood glucose values 510 may represent values measured by the electronic device 101 and second blood glucose values 520 may represent values measured by the external electronic device.

According to an embodiment, the external electronic device may measure the blood glucose using the biometric information sensor 201 or a sensor other than the biometric information sensor 201. The external electronic device may include, for example, at least one of a blood analyzer or a self-monitoring blood glucose measurement (SMBG) that measures the blood glucose through blood sampling. The external electronic device may perform the same or similar operation as an operation of at least one of a mobile device 601 or a measuring device 610 in FIG. 6 to be described below.

The blood glucose may be one of indicators of a user's health status. Information associated with the blood glucose may include, for example, at least one of a glucose tolerance, a glycemic index (GI), or a glycemic load (GL). The glucose tolerance is a measurement of glucose digestion or gluco-regulation ability of the user. The glycemic index may indicate a speed of absorption of saccharinity after the user has consumed a food containing the saccharinity (or carbohydrate). Even when the user consumes a food containing the same amount of saccharinity, the speed of absorption of the saccharinity may be different depending on a form (or a quality) of the saccharinity. Because the glycemic index may be measured on the basis of 50 g of the carbohydrate, the glycemic index of a food with a low carbohydrate proportion may be relatively high compared with an amount the food intake. The glycemic load, which is the glycemic index multiplied by a weight (unit: g) of the carbohydrate contained in the food and divided by 100, is an index in consideration of the amount of the food intake. The glycemic load may be used to account for changes in the blood glucose depending on the amount of intake, which is not included in the glycemic index. The electronic device 101 may obtain the information associated with the blood glucose by measuring the blood glucose of the user. The electronic device 101 may provide the user with information about the health status of the user (e.g., digestibility, blood glucose load, or metabolic status) or information about the food (e.g., glycemic index or glycemic load). For example, the blood glucose may be measured based on at least one of a blood glucose value (e.g., the first blood glucose values 510) based on the measurement time, an area under the curve (AUC), or a slope of a change amount of the blood glucose value.

According to an embodiment, because the blood glucose may change depending on a user's condition (e.g., meal state or sleep state), the blood glucose may need to be measured whenever the user's condition changes. For example, the blood glucose value may be lowest in an empty-stomach state (e.g., a first time point 512) and the blood glucose value may be highest at a time point (e.g., a second time period 514) one hour after the meal. Because an electronic device (e.g., the electronic device 101 in FIG. 1) may measure the blood glucose of the user while worn on the body part (e.g., wrist) of the user, the blood glucose may be monitored at a predetermined period of time. The electronic device 101 may sense whether an event associated with the blood glucose measurement occurs based on the monitored result.

According to an embodiment, the event associated with the blood glucose measurement may include a meal event or a sleep event, depending on the status of the user. For example, the electronic device 101 may identify at least one of a time point (e.g., a fourth time point 550) at which the blood glucose is equal to or above a predetermined threshold value or a time point at which a slope of the blood glucose values increases sharply to sense the meal event. According to an embodiment, the electronic device 101 may sense the meal event based on at least one of a biological signal (e.g., heart rate) of the user or a movement of the user sensed by the motion sensor (e.g., at least one of the acceleration sensor or the gyro sensor) in addition to the blood glucose value. According to an embodiment, the electronic device 101 may sense the meal event based on at least one of the blood glucose value, the biological signal, or the movement of a user. In another example, the electronic device 101 may determine that the sleep event has occurred after a predetermined time (e.g., 8 hours) has elapsed since the sleep of the user was sensed. When the sleep event is sensed, it may mean that the user is in the empty-stomach state (e.g., the time point 512).

According to an embodiment, because an accuracy of the blood glucose measurement may be reduced due to a blood glucose measurement environment (e.g., at least one of the user's movement, the ambient environment (e.g., illumination environment), or a wearing condition) of the electronic device 101, the electronic device 101 may guide the user to measure the blood glucose via the external electronic device when the event associated with the blood glucose measurement occurs. For example, when the fourth time point 550 indicates a time point of 30 minutes after the meal, the electronic device 101 may guide the user to measure the blood glucose via the external electronic device at least one time point of the current time point (e.g., 550), the time point (e.g., 514) one hour after the meal, or the time point (516) three hours after the meal.

According to an embodiment, the electronic device 101 may use the second blood glucose values 520 measured by the external electronic device to calibrate the first blood glucose values 510 measured by the electronic device 101. For example, the electronic device 101 may replace, with the second blood glucose values 520, a blood glucose value of the first blood glucose values 510, corresponding to a time point (e.g., at least one of 512, 514, or 516) at which the blood glucose is measured by the external electronic device. The electronic device 101 may generate the second graph 502 in which at least some of the first blood glucose values 510 are calibrated based on the second blood glucose values 520. The electronic device 101 may provide the user with the information associated with the blood glucose based on the blood glucose values represented by the second graph 502.

FIG. 5 illustrates the embodiment in which the electronic device 101 measures the blood glucose, but an embodiment in which the electronic device 101 measures a different biological signal may be applied on the same principle. For example, the electronic device 101 may monitor a user's blood pressure via the biometric information sensor 201 while being worn on the body part of the user. The electronic device 101 may sense an event associated with a blood pressure measurement. The event associated with the blood pressure measurements may occur, for example, at a predetermined time (e.g., within 2 minutes) after an end of an exercise. According to an embodiment, the electronic device 101 may sense the event associated with the blood pressure measurement by measuring the user's movement using a sensor (e.g., the acceleration sensor or the gyro sensor) other than the biometric information sensor 201.

Figure 6:
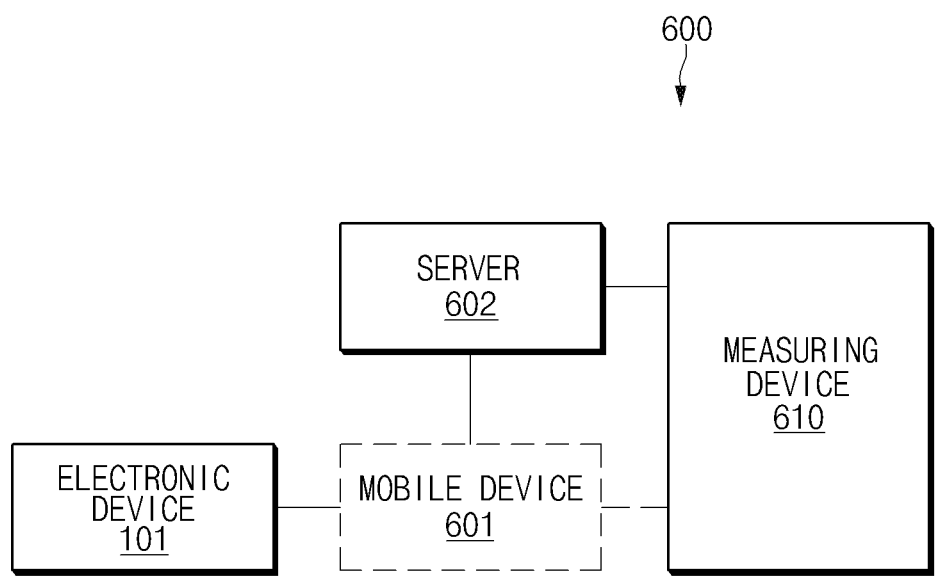
FIG. 6 illustrates a communication system for measuring a biological signal according to certain embodiments.

FIG. 6 illustrates a communication system 600 for measuring a biological signal according to certain embodiments.

Referring to FIG. 6, a server 602 may store data associated with the biological signal. The data associated with the biological signal may be, for example, at least one of a biological signal value measured by the electronic device 101 (e.g., the first blood glucose values 510 in FIG. 5), a biological signal value (e.g., the second blood glucose values 520 in FIG. 5) measured by the mobile device 601 or the measuring device 610, a calibrated biological signal value (e.g., the blood glucose values represented by the second graph 502 in FIG. 5), or information generated based on the calibrated biological signal (e.g., the glucose tolerance, the glycemic index, or the glycemic load). The electronic device 101 may secure a memory space by measuring the biological signal and storing the data associated with the biological signal in the server 602.

According to an embodiment, the measuring device 610 (e.g., a blood glucose meter) may perform the same operation as the operation of the external electronic device in FIG. 5. For example, the measuring device 610 may include at least one of the blood analyzer or the SMBG. When the event associated with the biological signal measurement occurs, the electronic device 101 may guide the user to measure the biological signal via the measuring device 610.

According to an embodiment, the mobile device 601 may be at least one of a portable communication device (e.g., a smart phone or a tablet), a computer device, or a portable multimedia device. The electronic device 101 may be connected to the mobile device 601 via a wireless communication protocol. The wireless communication protocol may be based on the first network 198 or the second network 199 in FIG. 1, for example. In another example, the wireless communication protocol may be based on at least one of a Bluetooth low energy (BLE), an ultra-wide band (UWB), and a near field communication (NFC).

According to an embodiment, the electronic device 101 may transmit or receive data with the server 602 or the measuring device 610 via the mobile device 601. For example, when the biological signal is measured by the measuring device 610, the measuring device 610 may transmit the measured biological signal value to the electronic device 101 via the mobile device 601. Alternatively, the mobile device 601 may deliver the information (e.g., the glucose tolerance, the glycemic index, or the glycemic load) generated by the electronic device 101 to the server 602. According to another embodiment, the mobile device 601 may store the data associated with the biological signal on behalf of the server 602, and may measure the biological signal value on behalf of the measuring device 610.

According to an embodiment, the communication system 600 may not include the mobile device 601. In this case, the electronic device 101 may perform wireless communication with the server 602 or the measuring device 610 based on the wireless communication protocol. For example, when the measuring device 610 is connected to the server 602 via a wired network or a wireless network and the server 602 stores data associated with biological signals for a plurality of users using the measuring device 610, the server 602 may store user account information of the electronic device 101. When the event associated with the measurement of the biological signal occurs, the electronic device 101 may transmit a message requesting the measurement of the biological signal to the server 602. The server 602 may identify the electronic device 101 based on the stored user account information and deliver the user account information of the electronic device 101 to the measuring device 610. The measuring device 610 may transmit the measured biological signal value to the server 602. In another example, the electronic device 101 may sense that the measuring device 610 is located within a predetermined threshold distance based on the short-distance wireless communication protocol (e.g., at least one of the BLE, the UWB, or the NFC) and directly transmit the user account information to the measuring device 610 based on the wireless communication protocol.

Figure 7A:
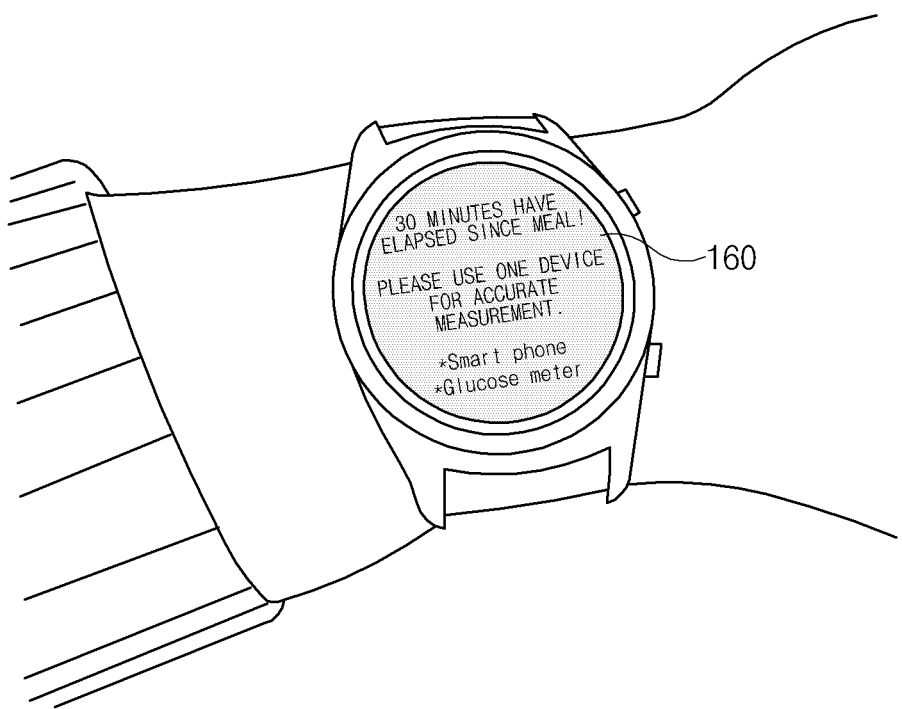
FIG. 7A illustrates a user interface (UI) of an electronic device that guides a measurement of a biological signal according to certain embodiments.

FIG. 7A illustrates a UI of the electronic device 101 that guides a measurement of a biological signal according to certain embodiments.

Referring to FIG. 7A, the electronic device 101 may display a UI that guides a measurement of the biological signal (e.g., the blood glucose) via the display device 160. For example, when the event (e.g., at the time point 30 minutes after the meal) associated with the blood glucose measurement occurs, the electronic device 101 may display text (e.g., "30 minutes have elapsed since the meal! Please use one device for an accurate measurement") that guides the blood glucose measurement via the display device 160.

According to another embodiment, the electronic device 101 may output sound via an audio module (e.g., 305 and 308 in FIGS. 3A and 3B) or output vibration via a haptic module (e.g., 179 in FIG. 1) when the event associated with the blood glucose measurement is detected. According to another embodiment, the electronic device 101 may output at least two of the UI, the sound, or the vibration at the same time.

According to an embodiment, the electronic device 101 may, on the display device 160, display a list of external electronic devices (e.g., a smartphone or a blood glucose meter) that may measure the blood glucose. For example, the smartphone may mean the mobile device 601 in FIG. 6, and the blood glucose meter may mean the measuring device 610 in FIG. 6. According to an embodiment, the electronic device 101 may display the external electronic devices on the list in an order of priority of the external electronic devices. The priority of the external electronic devices may be determined based on at least one of, for example, a distance between the external electronic device and the electronic device 101, a recent measurement history, or an accuracy of the measurement.

Although not illustrated in FIG. 7A, according to an embodiment, the electronic device 101 may, in response to a user input of selecting one external electronic device from the displayed list, display information associated with the external electronic device via the display device 160. The information associated with the external electronic device may include, for example, at least one of a location of the external electronic device, a usable state, or a type of a sensor that the external electronic device includes.

Figure 7B:
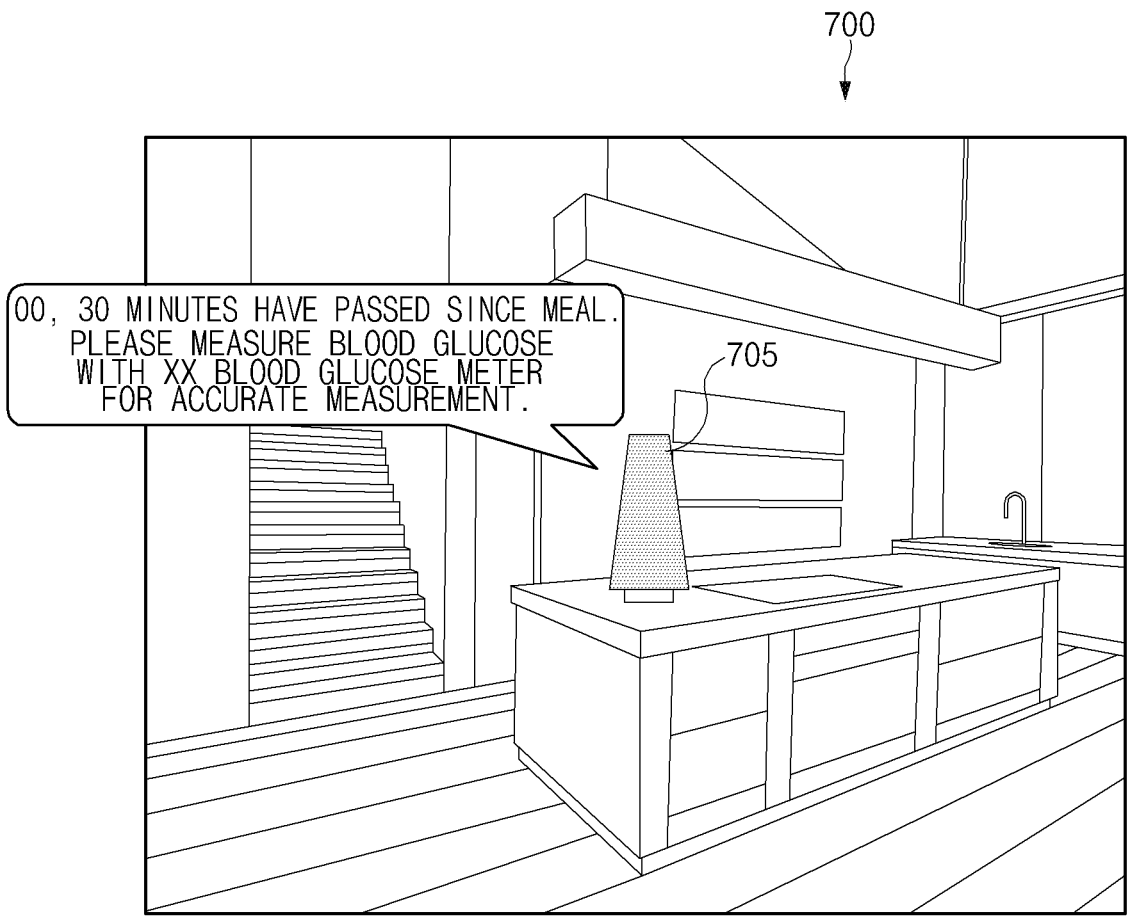
FIG. 7B illustrates a UI of an internet of things (IoT) device that guides a measurement of a biological signal according to certain embodiments.

FIG. 7B illustrates a UI of an IoT device 705 that guides a measurement of a biological signal according to certain embodiments.

Referring to FIG. 7B, the IoT device 705 may be a home appliance (e.g., a speaker, a television, a refrigerator, or a washing machine) disposed in an interior space 700. According to an embodiment, the IoT device 705 may be connected to the electronic device 101 via a wireless communication protocol. The wireless communication protocol may be based, for example, on at least one of the first network 198, the second network 199, the BLE, the UWB, or the NFC in FIG. 1. According to another embodiment, the IoT device 705 may be connected via the wireless communication protocol with at least one of the mobile device 601 or the server 602 in FIG. 6.

According to an embodiment, when the event (e.g., at the time point 30 minutes after the meal) associated with the measurement of the blood glucose occurs, the electronic device 101 may transmit information associated with the event to the IoT device 705 (e.g., an AI-enabled speaker). The information associated with the event may include, for example, at least one of a time point at which the event occurred, a name of the external electronic device, or a location of the external electronic device. According to another embodiment, the server 602 in FIG. 6 may transmit the information associated with the event to the IoT device 705. The IoT device 705 may output a sound (e.g., "Mr./Mrs. 00, 30 minutes have passed since the meal. Please measure the blood glucose with an XX blood glucose meter for an accurate measurement.") that guides the blood glucose measurement based on the information associated with the event.

According to another embodiment, when the electronic device 101 is detached from the body part of the user after the event associated with the measurement of the biological signal is sensed, the electronic device 101 may transmit the information associated with the event to the IoT device 705.

According to another embodiment, a server 605 may transmit the information associated with the event to the IoT device 705 after a predetermined time has elapsed since the event associated with the measurement of the biological signal occurred. For example, when the meal event (e.g., at the time point 30 minutes after the meal) occurs, the server 605 may transmit the information associated with the event to the IoT device 705 at the time point 30 minutes after the meal event.

Figure 8:
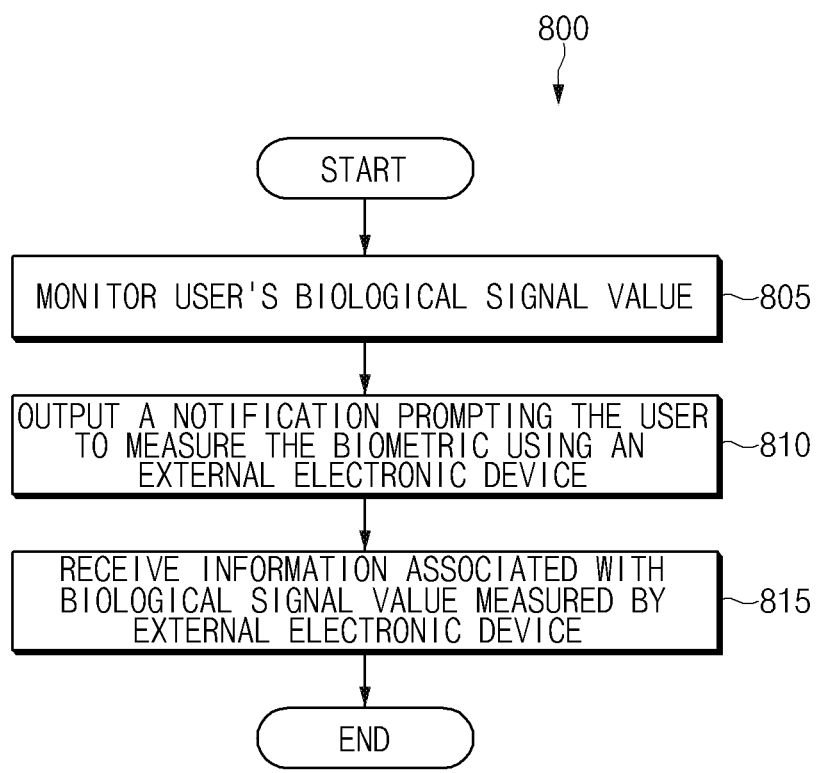
FIG. 8 illustrates an operational flowchart of an electronic device that calibrates a biological signal value according to certain embodiments.

FIG. 8 illustrates an operational flowchart 800 of the electronic device 101 that calibrates a biological signal value according to certain embodiments. In embodiments to be described below, operations illustrated in FIG. 8 or another operational flowchart may be performed by the electronic device 101 or by the processor 120.

Referring to FIG. 8, in operation 805, the electronic device 101 may monitor the user's biological signal value. The electronic device 101 may monitor the biological signal value using the biometric information sensor 201 while the electronic device 101 is worn by user, or otherwise coupled on a body part (e.g., the wrist) of the user via the attachment member (e.g., 350 and 360 in FIG. 3A). According to an embodiment, the electronic device 101 may periodically monitor the biological signal value at predetermined time intervals (e.g., 1 minute, 2 minutes, 5 minutes, or 10 minutes).

In operation 810, the electronic device 101 may prompt the user to obtain a measurement of the biological signal using an external electronic device (e.g., the mobile device 601 or the measuring device 610 in FIG. 6) based on the monitored biological signal value. According to an embodiment, the electronic device 101 may display, via the display device 160 (or via the display 320) a UI notification that prompts the user to measure the biological signal using the external electronic device. In another example, the electronic device 101 may output sound via an audio module (e.g., 305 and 308 in FIGS. 3A and 3B) or may output vibration via a haptic module (e.g., 179 in FIG. 1) to indicate the same to the user. According to an embodiment, the electronic device 101 may output at least two of the UI notification, the sound notification, or the vibration. According to another embodiment, the electronic device 101 may prompt, via an IoT device (e.g., 705 in FIG. 7) that is communicatively connected with the electronic device 101 via the wireless communication, the user to measure the biological signal using the external electronic device, using some output by the IoT device.

In operation 815, the electronic device 101 may receive the biological signal value measured by the external electronic device. According to an embodiment, the electronic device 101 may receive the biological signal value measured by the external electronic device from the external electronic device or from another electronic device (e.g., the mobile device 601 or the server 602), via wired or wireless transmission.

According to an embodiment, the electronic device 101 may provide a reception notification to the user in response to reception of the biological signal value, as measured by the external electronic device. For example, the electronic device 101 may display a UI notification indicating the reception of the biological signal value, via the display device. In another example, the electronic device 101 may output a sound notification via the audio module, or output a vibrational notification via the haptic module. According to an embodiment, the electronic device 101 may output at least two of the UI, the sound, or the vibration notifications.

According to an embodiment, the electronic device 101 may display the biological signal value measured by the external electronic device and the biological signal value monitored by the electronic device 101 together via the display device. For example, the electronic device 101 may display the first graph 501 illustrated in FIG. 5.

According to an embodiment, the electronic device 101 may calibrate the local biometric sensor which monitored the local biological signal value, based on the biological signal value measured by the external electronic device. For example, the electronic device 101 may generate the second graph 502 based on the first graph 501 in FIG. 5.

According to an embodiment, when the biological signal value is calibrated, the electronic device 101 may notify the user of the calibration of the biometric sensor and the corresponding biological signal value. For example, the electronic device 101 may display a UI screen including the second graph 502 via the display device. In another example, the electronic device 101 may output a sound notification via the audio module or output the vibration via the haptic module. According to an embodiment, the electronic device 101 may output at least two of the UI, the sound, or the vibration notifications.

Figure 9:
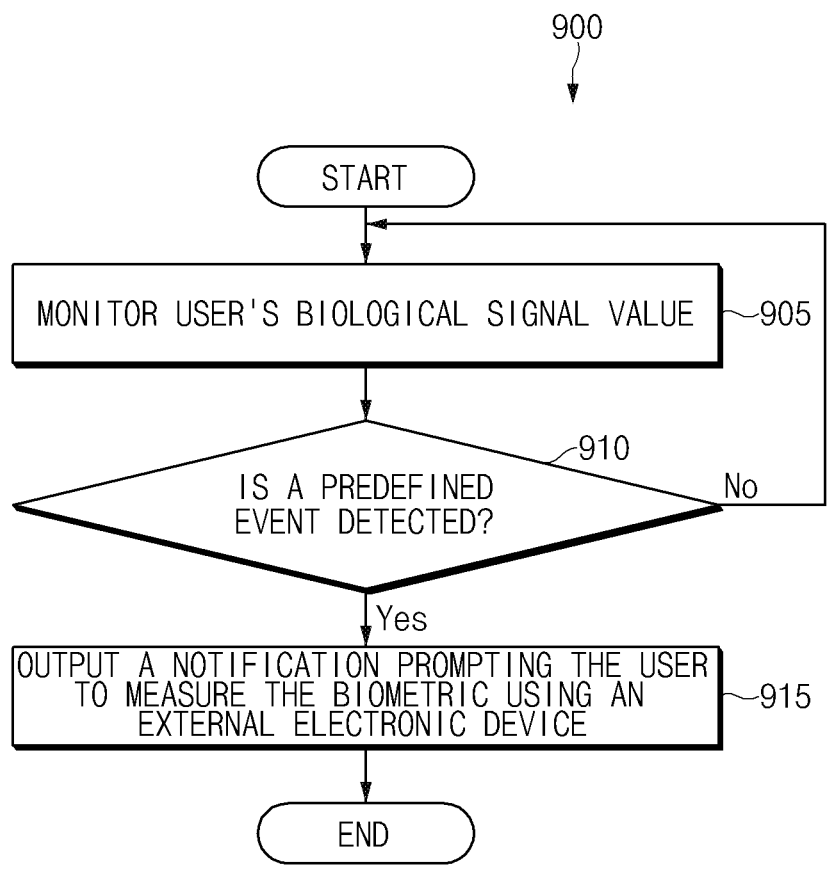
FIG. 9 illustrates an operational flowchart of an electronic device that guides a measurement of a biological signal in response of an occurrence of an event, according to various embodiment.
Figure 10:
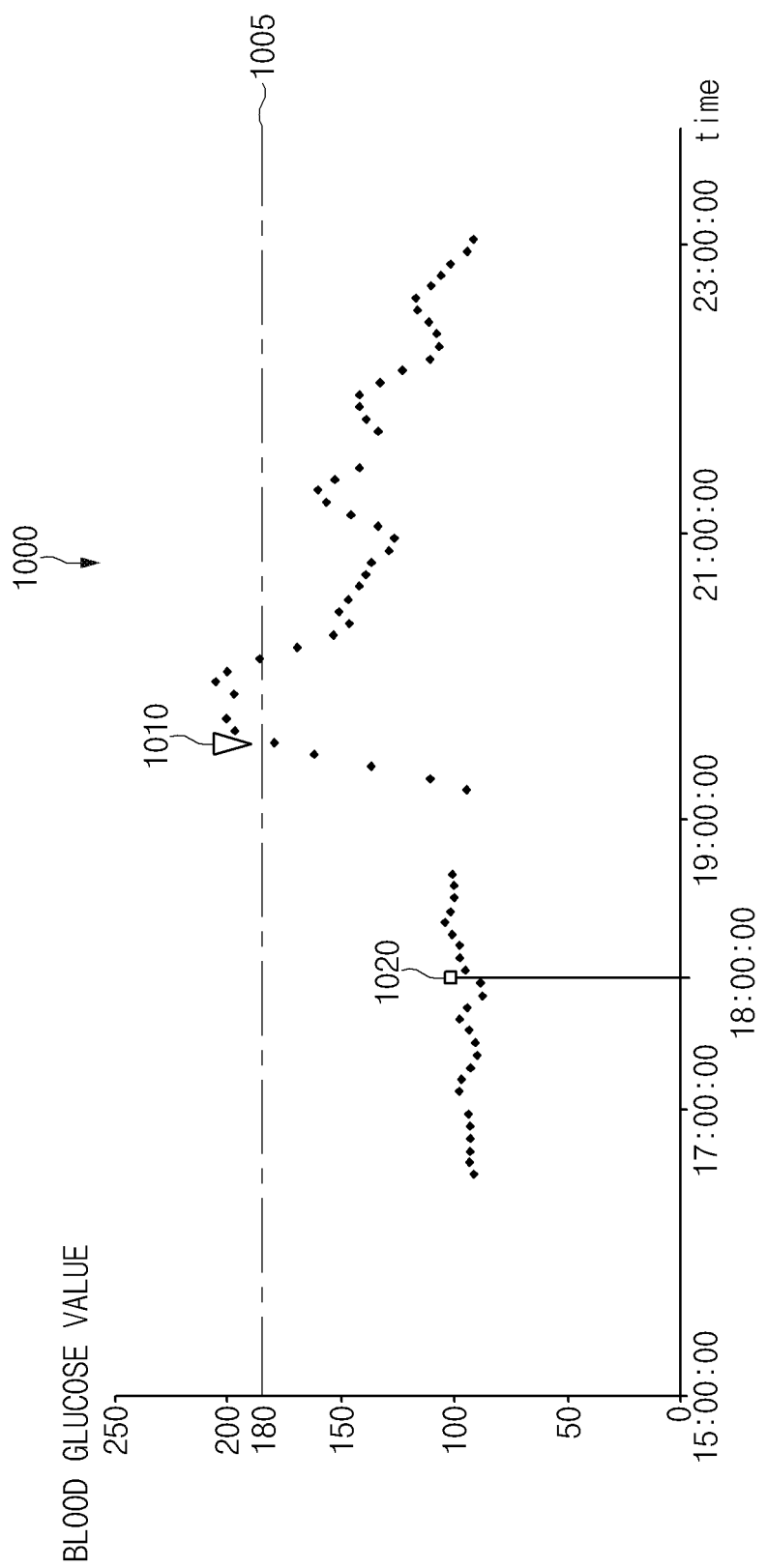
FIG. 10 illustrates a graph illustrating a time point at which an event occurred, according to certain embodiments.

FIG. 9 illustrates an operational flowchart 900 of the electronic device 101 that guides a measurement of a biological signal in response of an occurrence of an event, according to various embodiment. FIG. 10 illustrates a graph

1000 illustrating a time point at which an event occurred, according to certain embodiments. The operational flowchart 900 illustrated in FIG. 9 may be an embodiment of the operations 805 and 810 in FIG. 8.

Referring to FIG. 9, in operation 905, the electronic device 101 may monitor the user's biological signal value (e.g., the operation 805 in FIG. 8).

In operation 910, the electronic device 101 may determine whether a predefined event associated with the measurement of the biological signal occurs. When the biological signal tracks blood glucose, an example of a predefined event associated with the measurement of the biological signal may include, for example, at least one of a caloric intake event (e.g., a meal) or a resting state event (e.g., a sleep event). When the biological signal includes blood pressure, the predefined event associated with the measurement of the biological signal may occur, for example, at a time point in which a predetermined time has elapsed after the termination of a period of exercise.

According to an embodiment, the electronic device 101 may detect the meal event based on at least one of a time point at which the blood glucose is equal to or above the predetermined threshold value, or a time point at which the rate of change (e.g., a slope) in current blood glucose values increases sharply. For example, referring to the graph 1000 in FIG. 10, the electronic device 101 may identify a time point (e.g., a time point 1010) at which the blood glucose value measured by the biometric information sensor 201 is equal to or above a threshold value 1005 (e.g., 180 mg/dL) or a time point at which the slope of the change amount of the blood glucose value is equal to or above a threshold value (e.g., 1.5 mg/DL per minute) to sense the meal event. According to another embodiment, the electronic device 101 may sense the meal event via the IoT device connected to the electronic device 101 via a wired network or a wireless network. The IoT device may be, for example, the IoT device 705 in FIG. 7 or a separate IoT device. For example, when the user opens a door of a refrigerator or takes out a food placed in the refrigerator, the electronic device 101 may receive, via a wireless communication protocol, information indicating that the user is preparing the meal from the refrigerator. At the same time that information indicating that the user is preparing the meal, or when a predetermined time has elapsed since the information was received, the electronic device 101 may determine that the meal event has occurred.

According to an embodiment, the sleep event may occur at a predetermined time (e.g., 8 hours) after the user's sleep is sensed. According to an embodiment, the electronic device 101 may determine the user's sleep based on at least one of the heart rate of the user measured via the biometric information sensor 201 and the movement of the user measured via the motion sensor (e.g., at least one of the acceleration sensor or the gyro sensor). The electronic device 101 may determine that the sleep event has occurred at a time point (e.g., 1020) at which a predetermined time has elapsed since the user's sleep was sensed.

When the event associated with the measurement of the biological signal is not sensed, the electronic device 101 may perform the operations 905 and 910 repeatedly. When the event associated with the measurement of the biological signal is sensed, in operation 915, the electronic device 101 may prompt the user to measure the biological signal using the external electronic device (e.g., the operation 810 in FIG. 8).

Figure 11:
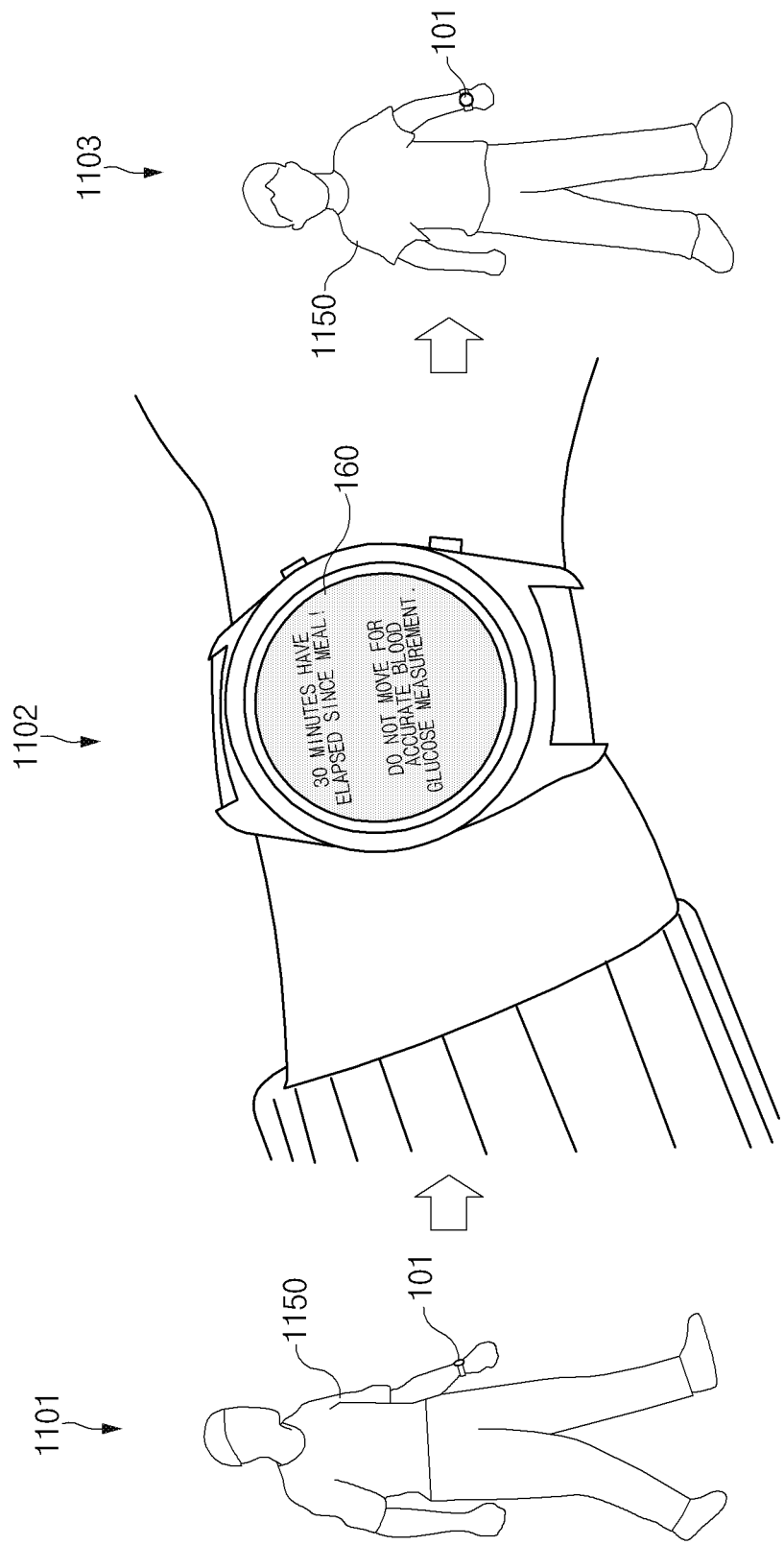
FIG. 11 illustrates a UI that guides a biological signal measurement by an electronic device 101 according to certain embodiments.

FIG. 11 illustrates a UI that guides a biological signal measurement by the electronic device 101 according to certain embodiments.

Referring to FIG. 11, when the event associated with the measurement of the biological signal is sensed, the electronic device 101 may guide the user to perform an accurate measurement by the electronic device 101.

In operation 1101, when a user 1150 moves while the electronic device 101 is worn on a body part (e.g., a wrist) of the user 1150, the electronic device 101 may sense a movement of the user 1150 via a motion sensor (e.g., at least one of a gyro sensor or an acceleration sensor).

When the event (e.g., at least one of the meal event or the sleep event) associated with the measurement of the biological signal occurs while the movement of the user 1150 is detected, in operation 1102, the electronic device 101 may display, via the display 160, a UI (e.g., "Do not move for an accurate blood glucose measurement.") that guides the user not to move. According to another embodiment, the electronic device 101 may guide the user to fix an attachment member (e.g., 350 and 360 in FIG. 3A) of the electronic device 101. According to another embodiment, when an ambient brightness of the electronic device 101 is equal to or above a predetermined threshold value, the electronic device 101 may guide the user to reduce a brightness of a surrounding light.

When the movement of the user 1150 is not sensed, in operation 1103, the electronic device 101 may measure the biological signal via the biometric information sensor 201. Because a biological signal value measured in the operation 1103 is more accurate than a biological signal value measured in the operation 1101, the electronic device 101 may calibrate the biological signal value measured in the operation 1101 based on the biological signal value measured in the operation 1103.

Figure 12:
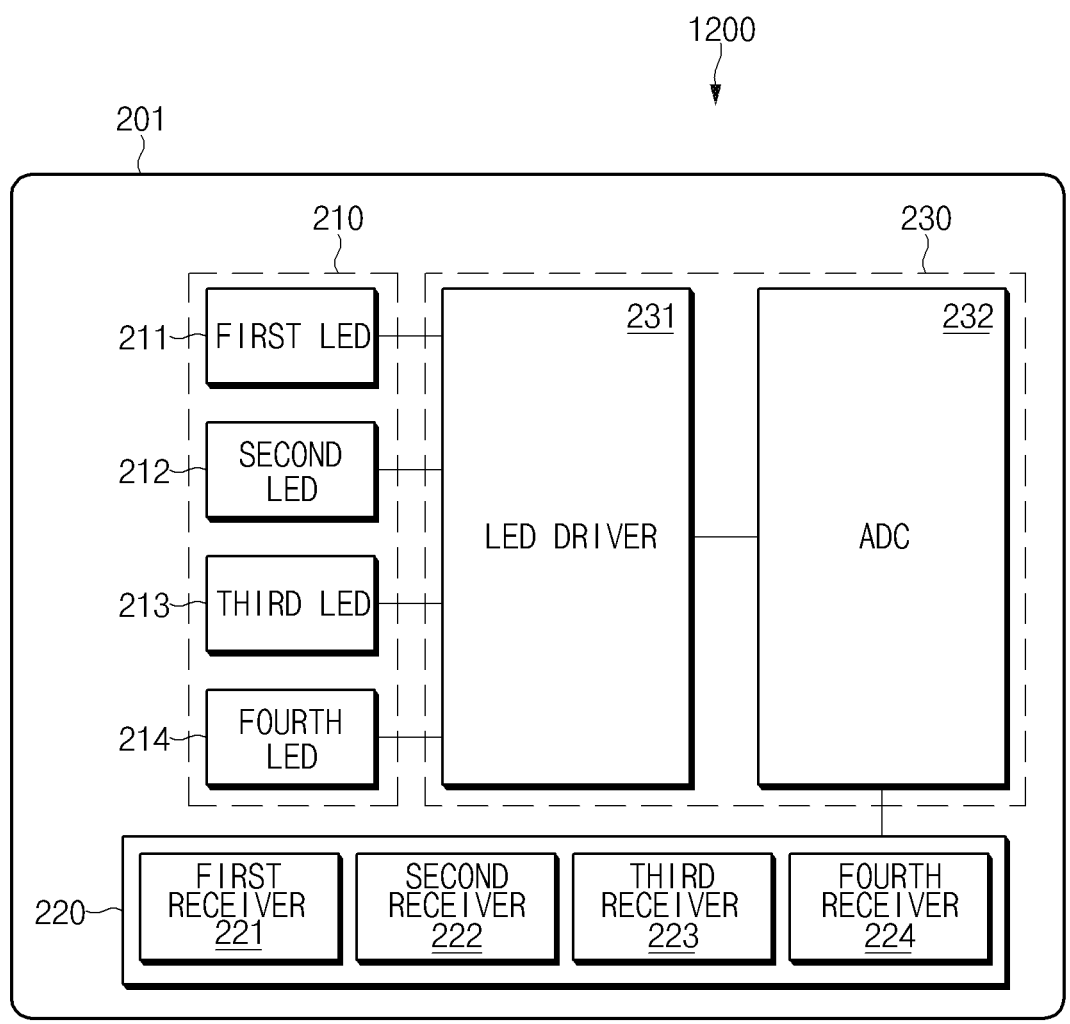
FIG. 12 illustrates a block diagram of a biometric information sensor according to an embodiment.

FIG. 12 illustrates a block diagram 1200 of the biometric information sensor 201 according to an embodiment.

Referring to FIG. 12, the emitter 210 may include at least one of a first LED 211, a second LED 212, a third LED 213, or a fourth LED 214. The number of the LEDs included in the emitter 210 is and the number of the LEDs in the emitter 210 is not limited thereto. According to an embodiment, the first LED 211 may be a green LED, the second LED 212 may be a blue LED, the third LED 213 may be an infrared LED, and the fourth LED 214 may be a red LED. According to an embodiment, the emitter 210 may include at least one LED that may illuminate a wavelength corresponding to at least one of the blue, the green, the red, and the infrared. For example, the emitter 210 may include one LED that may simultaneously illuminate all wavelengths respectively corresponding to the blue, the green, the red, and the infrared rays.

According to certain embodiments, the signal processor 230 may include an LED driver 231 and an analog to digital converter (ADC) 232. The signal processor 230 may further include other components (e.g., an amplifier, a filter, and/or a memory, or the like) not illustrated in FIG. 12.

According to certain embodiments, the LED driver 231 may control the emitter 210 (e.g., at least one of the first LED 211, the second LED 212, the third LED 213, or the fourth LED 214) in a predetermined state. For example, a processor (e.g., the processor 120 in FIG. 2) may control the emitter 210 using the LED driver 231. According to an embodiment, the LED driver 231 may drive the emitter 210 in an always-on state. According to an embodiment, the LED driver 231 may turn the emitter 210 on for a predetermined time (e.g., 1 μs to 10 ms). According to an embodiment, the LED driver 231 may flicker the emitter 210 at a predetermined period of time. For example, the LED driver 231 may control the emitter 210 in a sensing state (e.g., flickering at a sensor sample rate (e.g., 10 to 1000 Hz)).

According to certain embodiments, the ADC 232 may convert an analog signal sensed by the receiver 220 into a digital signal. According to certain embodiments, the receiver 220 may include a plurality of light receiving elements (e.g., photo detectors). According to an embodiment, the receiver 220 may include a first receiver 221, a second receiver 222, a third receiver 223, and/or a fourth receiver 224. The four receivers are illustrative, and the receiver 220 may include a plurality of receivers.

Figure 13:
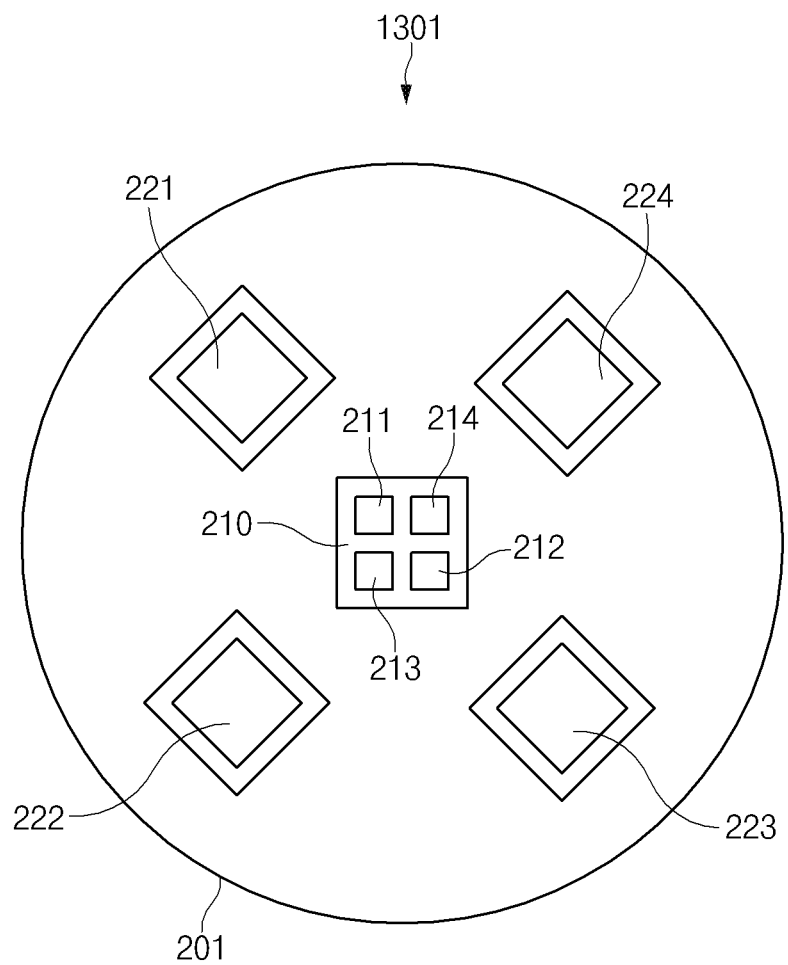
FIG. 13 illustrates a structure of a biometric information sensor according to certain embodiments.

FIG. 13 illustrates a structure 1301 of the biometric information sensor 201 according to certain embodiments.

Referring to FIG. 13, the biometric information sensor 201 may include the plurality of receivers 221, 222, 223, and/or 224 respectively positioned adjacent to vertices of the emitter 210.

According to certain embodiments, the biometric information sensor 201 may sense an oxygen saturation of an external object using an infrared LED (e.g., the third LED 213) and a red LED (e.g., the fourth LED 214). According to an embodiment, an electronic device (e.g., the electronic device 101 in FIG. 2) may simultaneously or sequentially illuminate the infrared LED (e.g., the third LED 213) and the red LED (e.g., the fourth LED 214) and detect red or infrared light using at least one receiver at the same distance from the infrared LED (e.g., the third LED 213) and the red LED (e.g., the fourth LED 214). For example, the electronic device 101 may detect the red light and the infrared light using the first receiver 221 and/or the third receiver 223. In another example, the electronic device 101 may detect the infrared light using the first receiver 221 and the red light using the fourth receiver 224.

According to certain embodiments, the electronic device 101 may measure a blood glucose of the external object using a receiver located at a position where distances to a blue LED (e.g., the second LED 212) and an infrared LED (e.g., the third LED 213) of the biometric information sensor 201 are different. According to an embodiment, the electronic device 101 may sense the blood glucose using a receiver relatively close to the blue LED (e.g., the second LED 212) and relatively far away from the infrared LED (e.g., the third LED 213). For example, the biometric information sensor 201 may measure the blood glucose by sensing blue light and infrared light using the third receiver 223 and/or the fourth receiver 224.

According to certain embodiments, the electronic device 101 may sense heart rate information using all of the four receivers 221, 222, 223, and 224. The electronic device 101 may, for example, obtain more accurate heart rate information or blood pressure information using the plurality of receivers. According to an embodiment, the electronic device 101 may obtain blood pressure information of the external object using the plurality of receivers. The electronic device 101 may illuminate a green LED (e.g., the first LED 211) and detect green light using the plurality of receivers. For example, the electronic device 101 may accumulate and/or compare data of optical signals respectively detected by the plurality of receivers to obtain the blood pressure information. The electronic device 101 may obtain the blood pressure information based on an average or summation of the optical signals respectively detected by the plurality of receivers. The electronic device 101 may obtain the blood pressure information using an optical signal having a quality equal to or above a predetermined value (e.g., a SNR equal to or above a predetermined value) among optical signals detected by the plurality of receivers. According to an embodiment, the electronic device 101 may obtain heart rate information of the external object using the plurality of receivers. The electronic device 101 may simultaneously or sequentially illuminate a green LED (e.g., the first LED 211) and an infrared LED (e.g., the third LED 213) and detect green light and infrared light using the plurality of receivers. The electronic device 101 may obtain the heart rate information based on an average or summation of optical signals detected by the plurality of receivers. The electronic device 101 may obtain the heartbeat information using an optical signal having a quality equal to or above a predetermined value (e.g., a SNR equal to or above a predetermined value) among the optical signals detected by the plurality of receivers.

As described above, an electronic device (e.g., 101 in FIG. 3A) may include a housing (e.g., 310 in FIG. 3A), a display (320 in FIG. 4A) visible through a first portion of the housing, a photoplethysmogram (PPG) sensor (201 in FIG. 2) exposed through a second portion of the housing, a wireless communication circuit (e.g., 190 in FIG. 2), a processor (e.g., 120 in FIG. 2) operatively connected to the display, the PPG sensor, and the wireless communication circuit, and a memory (e.g., 130 in FIG. 2) operatively connected to the processor, in which the memory may store instructions, and when the instructions are executed, the processor may monitor blood glucose values of a user using the PPG sensor, display, via the display, a notification informing the user to measure blood glucose values using an external electronic device (e.g., 601 or 610 in FIG. 6) at least partially based on the monitored blood glucose values, and receive the blood glucose values measured by the external electronic device using the wireless communication circuit.

According to an embodiment, the instructions may allow the processor to calibrate the monitored blood glucose values at least partially based on the received blood glucose values.

According to an embodiment, the instructions may allow the processor to store information associated with the calibrated blood glucose values in the memory, or transmit the information associated with the calibrated blood glucose values to the external electronic device or a server (602 in FIG. 6) using the wireless communication circuit.

According to an embodiment, the instructions may allow the processor to sense an occurrence of an event at least partially based on the monitored blood glucose values, and display the notification via the display in response to the occurrence of the event.

According to an embodiment, the instructions may allow the processor to detect the occurrence of the event when the monitored blood glucose values are equal to or above a selected value, and/or when a slope of a change amount of the monitored blood glucose values is equal to or above a threshold value.

According to an embodiment, the event may include at least one of a meal event or a sleep event.

According to an embodiment, the instructions may allow the processor to receive the blood glucose values measured by the external electronic device from the external electronic device or a server using the wireless communication circuit.

According to an embodiment, the electronic device of claim may further include an attachment structure (e.g., 350 and 360 in FIG. 3A) connected to a portion of the housing and coupled to a body part of the user.

As described above, a method of a wearable device (e.g., 101 in FIG. 3A) worn on a body part of a user may include monitoring blood glucose values of the user in every predetermined period of time, displaying a user interface (UI) for guiding the user to measure blood glucose values by an external electronic device at least partially based on the monitored blood glucose values, and receiving the blood glucose values measured by the external electronic device.

According to an embodiment, the receiving of the blood glucose values measured by the external electronic device may include receiving the blood glucose values measured by the external electronic device from the external electronic device or a server.

According to an embodiment, the method may further include calibrating at least some of the monitored blood glucose values at least partially based on the received blood glucose values.

According to an embodiment, the method may further include storing information associated with the calibrated blood glucose values in a memory of the wearable device, or transmitting the information associated with the calibrated blood glucose value to the external device or a server.

According to an embodiment, the displaying of the UI may include sensing an event associated with a measurement of a blood glucose at least partially based on the monitored blood glucose values, and displaying the UI when the event associated with the measurement of the blood glucose is sensed.

According to an embodiment, the sensing of the event associated with the measurement of the blood glucose may include sensing the event associated with the measurement of the blood glucose at least partially based on a slope of a change amount of the monitored blood glucose values.

According to an embodiment, the sensing of the event associated with the measurement of the blood glucose may include sensing a sleep state of the user, and sensing the event associated with the measurement of the blood glucose at least partially based on the sensed sleep state and the monitored blood glucose values.

As described above, a wearable device (e.g., 101 in FIG. 3A) capable of being worn on a body part of a user may include at least one attachment member (e.g., 350 and 360 in FIG. 3A) capable of being detached from the body part of the user, a housing (e.g., 310 in FIG. 3A) coupled to the at least one attachment member, a display (e.g., 320 in FIG. 4A) visible through a first portion of the housing, a photoplethysmogram (PPG) sensor (e.g., 201 in FIG. 2) exposed through a second portion of the housing opposite to the first portion, a wireless communication circuit (e.g., 190 in FIG. 2) included in the housing, a processor (e.g., 120 in FIG. 2) operatively connected to the display, the PPG sensor, and the wireless communication circuit, and a memory (e.g., 130 in FIG. 2) operatively connected to the processor, in which the memory may store instructions, and when the instructions are executed, the processor may monitor blood glucose values of the user using the PPG sensor, display, via the display, a notification informing the user to measure blood glucose values using an external electronic device (e.g., 601 or 610 in FIG. 6) at least partially based on the monitored blood glucose values, receive the blood glucose values measured by the external electronic device using the wireless communication circuit, and calibrate the blood glucose values of the wearable device at least partially based on the received blood glucose values.

According to an embodiment, the instructions may allow the processor to detect an event at least partially based on the monitored blood glucose values, and display the notification via the display in response to the detection of the event.

According to an embodiment, the instructions may allow the processor to determine an occurrence of the event when the monitored blood glucose values are equal to or above a selected value.

According to an embodiment, the instructions may allow the processor to detect an occurrence of the event at least partially based on a slope of a change amount of the monitored blood glucose values.

According to an embodiment, the instructions may allow the processor to receive the blood glucose values measured by the external electronic device from the external electronic device or a server using the wireless communication circuit.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked.

The one or more instructions may include a code generated by a compiler or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

According to the embodiments disclosed in the disclosure, the electronic device may guide the user to measure the biological signal to induce the user to check a health status of the user.

According to the embodiments disclosed in the disclosure, the electronic device may use the information measured by the external electronic device to increase the accuracy of the biological signal measurement.

In addition, various effects, directly or indirectly understood through this document, may be provided.

While the disclosure has been shown and described with reference to certain embodiments thereof, it will be understood by those skilled in the art that various changes in form and details may be made therein without departing from the disclosure as defined by the appended claims and their equivalents.

What is claimed is:

1. An electronic device, comprising:
a housing;
a display visible through a first portion of the housing;
a photoplethysmogram (PPG) sensor exposed through a second portion of the housing;
a wireless communication circuit;
a processor operatively connected to the display, the PPG sensor, and the wireless communication circuit; and
a memory operatively connected to the processor, wherein the memory stores instructions executable by the processor to cause the electronic device to:
monitor first blood glucose values at a specified time interval using the PPG sensor;
based on the monitored first blood glucose values, identify whether a change amount of the monitored first blood glucose values is more than a threshold value,
determine whether specified time is elapsed after identifying that the change amount of the monitored first blood glucose values is more than the threshold value, and
in response to determining that the specified time is elapsed, display a notification on the display prompting measurement of blood glucose using an external electronic device.

2. The electronic device of claim 1,
wherein displaying the notification further includes:
detecting an occurrence of a predefined event, based at least partially on the first blood glucose values, and
displaying the notification via the display in response to detecting the occurrence of the predefined event.

3. The electronic device of claim 1, wherein the instructions are further executable by the processor to cause the electronic device to:
identify occurrence of a predefined event as detected by an Internet-of-Things (IoT) device communicably connected to the electronic device via the wireless communication circuit, and
in response to identifying the occurrence of the predefined event, display the notification on the display,
wherein the predefined event includes detecting, by the IoT device, opening of a door of the IoT device, which is transmitted to and received by the electronic device via the wireless communication circuit.

4. The electronic device of claim 1, further comprising:
an attachment structure adapted to couple a portion of the housing to a user of the electronic device.

5. The electronic device of claim 1, wherein the instructions are further executable by the processor to cause the electronic device to:
after displaying the notification, receive a transmission through the wireless communication circuit of a second blood glucose value as detected by the external electronic device; and
adjust the monitored first blood glucose values based on the second blood glucose value.

6. The electronic device of claim 5, wherein the instructions are further executable by the processor to cause the electronic device to:
calibrate the PPG sensor based at least partially on the first blood glucoses values and the second blood glucose value received from the external electronic device.

7. The electronic device of claim 6, wherein the instructions are further executable by the processor to cause the electronic device to:
store information associated with calibration of the PPG sensor in the memory; or
transmit the information associated with the calibration to the at least one of the external electronic device and a server, using the wireless communication circuit.

8. A method of a wearable electronic device, the method comprising:

when the wearable electronic device is coupled to a body part of a user, periodically monitoring first blood glucose values using a photoplethysmogram (PPG) sensor at a specified time interval;

based on the monitored blood glucose values, identifying whether the change amount of the monitored first blood glucose values is more than a threshold value;

determining whether specified time is elapsed after identifying that a change amount of the monitored first blood glucose values is more than the threshold value, and in response to determining that the specified time is elapsed, displaying a notification on a display prompting measurement of blood glucose using an external electronic device.

9. The method of claim 8, further comprising:

identifying occurrence of a predefined event as detected by an Internet-of-Things (IoT) device communicably connected to the electronic device via the wireless communication circuit, and in response to identifying the occurrence of the predefined event, displaying the notification on the display, wherein the predefined event includes detecting, by the IoT device, opening of a door of the IoT device, which is transmitted to and received by the electronic device via the wireless communication circuit.

10. The method of claim 8, further comprising:

detecting a sleep state of the user, in response to detecting the sleep state, displaying the notification on the display.

11. The method of claim 8, further comprising:

after displaying the notification, receiving a transmission through a wireless communication circuit of a second blood glucose value, as detected by the external electronic device; and adjusting the monitored first blood glucose values based on the second blood glucose value.

12. The method of claim 11, further comprising:

calibrating the PPG sensor based at least partially on the first blood glucose values and the second blood glucose value received from the external electronic device.

13. The method of claim 12, further comprising:

storing information associated with calibration of the PPG sensor in a memory, or transmitting the information associated with the calibration to the at least one of the external electronic device and a server, using the wireless communication circuit.

* * * * *